US012570657B2

(12) United States Patent
Klos et al.

(10) Patent No.: US 12,570,657 B2
(45) Date of Patent: Mar. 10, 2026

(54) MESYLATE SALTS OF HETEROCYCLIC CYTOKININS, COMPOSITIONS CONTAINING THESE DERIVATIVES AND USE THEREOF

(71) Applicant: UNIVERZITA PALACKEHO V OLOMOUCI, Olomouc (CZ)

(72) Inventors: Dardan Klos, Bernartice nad Odrou (CZ); Lucie Plihalova, Olomouc (CZ); Marek Zatloukal, Sumperk (CZ); Karel Dolezal, Hlubocky (CZ); Radoslav Koprna, Olomouc (CZ); Miroslav Strnad, Olomouc (CZ); Jan Walla, Olomouc (CZ); Jarmila Balonova, Velka Bystrice (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 572 days.

(21) Appl. No.: 17/925,709

(22) PCT Filed: Aug. 22, 2020

(86) PCT No.: PCT/CZ2020/050060

§ 371 (c)(1),
(2) Date: Nov. 16, 2022

(87) PCT Pub. No.: WO2021/233485

PCT Pub. Date: Nov. 25, 2021

(65) Prior Publication Data

US 2023/0192697 A1 Jun. 22, 2023

(30) Foreign Application Priority Data

May 17, 2020 (CZ) ................................ CZ2020-276

(51) Int. Cl.
*C07D 473/34* (2006.01)
*A01N 43/90* (2006.01)
*A01P 21/00* (2006.01)

(52) U.S. Cl.
CPC ........... *C07D 473/34* (2013.01); *A01N 43/90* (2013.01); *A01P 21/00* (2021.08); *C07B 2200/13* (2013.01)

(58) Field of Classification Search
CPC ....... C07D 473/34; A01N 43/90; A01P 21/00; C07B 2200/13
See application file for complete search history.

(56) References Cited

U.S. PATENT DOCUMENTS 8,552,013 B2 * 10/2013 Popa ....................... A61P 17/06 424/401
2019/0194207 A1 * 6/2019 de Roulet ............ C07D 473/34

FOREIGN PATENT DOCUMENTS

WO 2009003428 A2 1/2009
WO 2016095881 A1 6/2016

OTHER PUBLICATIONS

Kim, Dae-Kee, et al., Synthesis and Evaluation of 2-Amino-9-(3-hydroxymethyl-4-alkoxycarbonyloxybut-1-yl)purines as Potential Prodrugs of Penciclovir, 1998, J. Med. Chem., vol. 41, pp. 3435-3441. (Year: 1998).*
Berge, S.M. et al., Pharmaceutical Salts, Jan. 1977, Journal of Pharmaceutical Sciences, vol. 66, Issue 1, pp. 1-19. (Year: 1977).*
Duraisamy, Tamilselvi, et al.; “Supramolecular patterns in benzyladeninium p-toluenesulfonate”; CTA Crystallographica Section C. Crystal Structure Communications 2011; 67(5):192-194.
Huang, et al.; “An efficient synthesis of substituted cytosines and purines under focused microwave irradiation”; Tetrahedron, Elsevier Science Publishers 2007; 63(24):5323-5327.
International Search Report and Written Opinion for PCT/CZ2020/050060 dated Oct. 28, 2020.

* cited by examiner

*Primary Examiner* — Ali Soroush
*Assistant Examiner* — Andriae M Holy
(74) *Attorney, Agent, or Firm* — Notaro, Michalos & Zaccaria P.C.

(57) ABSTRACT

Mesylates of heterocyclic cytokinins of general formula I:

(I)

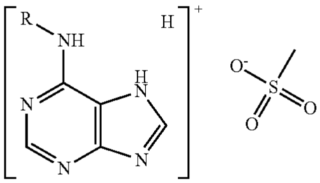

wherein R is selected from the group comprising C3-C15 cycloalkyl, furfuryl, allyl, 4-hydroxy-3-methylbut-2-en-1-yl, 3-methylbut-2-en-1-yl, 4-hydroxy-3-methylbutyl, 4-hydroxy-1,3-dimethylbut-2-en-1-yl, 4-hydroxy-1,3-dimethylbutyl, benzyl, wherein the cycloalkyl, allyl, benzyl and furfuryl may be unsubstituted or optionally substituted with 1 to 3 substituents selected from the group containing hydroxy, halogen, methyl, hydroxymethyl and methoxy, and salts, solvates and addition salts thereof. These compounds are particularly suitable for agricultural and biotechnological use, and their great advantage is increased water solubility as compared to the corresponding free bases of heterocyclic cytokinins.

3 Claims, 5 Drawing Sheets

(Coupled TwoTheta/Theta)

(Coupled TwoTheta/Theta)

MESYLATE SALTS OF HETEROCYCLIC CYTOKININS, COMPOSITIONS CONTAINING THESE DERIVATIVES AND USE THEREOF

FIELD OF ART

The invention relates to mesylate salts of heterocyclic cytokinins, their use in agricultural and biotechnological applications and compositions containing these derivatives.

BACKGROUND ART

Cytokinins (CKs) are adenine derivatives containing different substituents attached to the $N^6$-position of the heterocyclic molecule adenine. Depending on side chain structure, they are divided into two groups and referred to as isoprenoid and aromatic CKs. The isoprenoid cytokinins are a more abundant group of CKs in natural environment. Main representatives of the isoprenoid CKs are $N^6$-isopentenyladenine (iP) and its hydroxylated form, trans-zeatin (tZ). Both mentioned isoprenoid representatives are considered to be active at cytokinin receptors in Arabidopsis (Inoue et al., 2001, Nature 409, 1060-1063). Zeatin also exists in cis configuration (cZ) which shows a lower cytokinin activity (Spichal et al., 2004, FEBS Journal 276, 244-253.) but still it is an ubiquitous form in plants (Gajdošovà et al., 2011, J Exp Bot 62, 2827-2840). Reduction of the double bond in the isoprenoid side chain of zeatin can lead to formation of dihydrozeatin (DHZ), which shows lower biological activity in plant tissues than zeatin (Letham, 1963, Life Sci, 8:569-573). In addition to the free bases, which are the active forms, cytokinins are also present as ribosides (in which a ribose sugar is attached to the N9 of the purine ring) and ribotides (in which the ribose moiety contains a phosphate group). Cytokinins are plant-specific chemical messengers (hormones) that play a central role in the regulation of the plant cell cycle and numerous developmental processes.

Since the discovery of hydroxylated aromatic cytokinins topolins as naturally occurring aromatic cytokinins (Strnad 1997, Physiol Plant 101, 674-688), these new compounds have emerged as genuine alternatives to the long known CKs such as 6-benzylaminopurine (BAP), trans-zeatin (tZ) and kinetin (K) in plant tissue culture (PTC). Globally, the past 15 years has witnessed a surge in the use of topolins and their derivatives in research laboratories. Topolins, especially meta-topolin and its derivatives, have been employed for culture initiation, protocol optimization and for counteracting various in vitro induced physiological disorders (hyperhydricity, shoot tip necrosis, formation of chimeras, inhibition of root formation during acclimatization and premature senescence) in many plant species grown in in vitro culture. Many studies indicate the rising popularity and advantages (although not universal for all species) of topolins compared to other CKs (Adeyemi et al. 2012, Plant Tissue Organ Cult. 108: 1-16.). Cytokinins are unfortunatelly practically insoluble in water but have high cell membrane permeability. Low water solubility and slow dissolution rate are often limiting factors responsible for the low bioavailability of compounds, limiting their application possibilities. Despite the longknown fact that cytokinins have certain properties of growth regulatory compounds, no successful simple treatment regimens have been, or are, employed in the treatment of plants. One plausible explanation for this is probably the poor solubility and poor bioavailability as well as the rapid metabolism of cytokinins in their known forms.

Salts of active compounds may exist in different physical forms, including amorphous and crystalline forms. While amorphous form consists of a disordered arrangement of molecules, a crystalline form consists of an ordered arrangement of molecules in a repeating pattern to form a lattice. When a solid exists in two or more crystalline forms that have different arrangements and/or conformations of the molecules in the crystalline lattice, it is said to exhibit polymorphism and the different crystalline forms are called polymorphs. Polymorphs of solids may have different physical and solid-state chemical (reactivity) properties. Polymorphs differ in internal solid-state structure and, therefore, possess different chemical and physical properties, including packing, thermodynamic, spectroscopic, kinetic, interfacial and mechanical properties. These properties can have a direct impact on product quality/performance, including stability, dissolution, and bioavailability. The preparation of amorphous forms on an industrial scale is often problematic. Many processes used to prepare amorphous or crystalline forms of active pharmaceutical ingredients ("API") are not suitable for industrial scale. By crystallizing new cytokinin salts, a new solid state form of the compound having unique properties compared with existing solid forms of the cytokinin or its salt may be achieved. Crystallographic and spectroscopic properties of the individual forms are typically measured by X-ray powder diffraction (XRPD) and single crystal X-ray crystallography, among other techniques. Individual crystalline forms often also exhibit distinct thermal behavior e.g. different melting point.

DISCLOSURE OF THE INVENTION

The present invention provides mesylate salts of $N^6$-substituted adenine derivatives represented by general formula I (I)

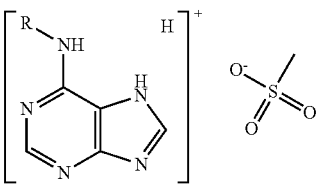

wherein R is selected from the group comprising C3-C15 cycloalkyl, furfuryl, allyl, 4-hydroxy methylbut-2-en-1-yl, 3-methylbut-2-en-1-yl, 4-hydroxy-3-methylbutyl, 4-hydroxy-1,3-dimethylbut en-1-yl, 4-hydroxy-1,3-dimethylbutyl, benzyl, wherein cycloalkyl, allyl, benzyl and furfuryl can be unsubstituted or optionally substituted with 1 to 3 substituents selected from the group comprising hydroxy, halogen, methyl, hydroxymethyl and methoxy, and salts, solvates and addition salts therof.

Mesylates of heterocyclic cytokinins of the general formula I of this invention also include any optically active isomers or mixtures thereof, including racemates.

Throughout this specification, and unless specifically indicated otherwise, the generic substituent names have the following meanings:

halogen denotes fluorine, bromine, chlorine, or iodine atom, hydroxy denotes the group —OH;

methyl denotes the group $—CH_3$;

methoxy denotes the group $—OCH_3$;

hydroxymethyl denotes the group $HO—CH_2—$

C3-C15 cycloalkyl denotes a monocyclic or polycyclic alkyl group containing 3 to 15 carbon atoms (preferably selected from cyclopropyl, cyclobutyl, cyclopentyl, cyclohexyl, cycloheptyl and adamantyl).

Preferred are compounds of general formula I selected from the group comprising 6-(2-hydroxycyclopropylamino) purine mesylate, 6-(3-hydroxycyclobutylamino)purine mesylate, 6-(3-methoxycyclobutylamino)purine mesylate, 6-(3-methoxycyclopentylamino)purine mesylate, 6-cyclohexylaminopurine mesylate, 6-(3-hydroxycyclohexylamino)purine mesylate, 6-(3-methoxycyclohexylamino)purine mesylate, 6-(3-hydroxyfurfurylamino)purine mesylate, 6-(4-hydroxyfurfurylamino)purine mesylate, 6-(5-hydroxyfurfurylamino)purine mesylate, 6-(3-methoxyfurfurylamino)purine mesylate, 6-(4-methoxyfurfurylamino)purine mesylate, 6-(5-methoxyfurfurylamino)purine mesylate, 6-(2-hydroxy-3-chlorobenzylamino)purine mesylate, 6-(2-hydroxy-5-chlorobenzylamino)purine mesylate, 6-(4-hydroxy-3-chlorobenzylamino)purine mesylate, 6-(3-hydroxy-5-chlorobenzylamino)purine mesylate, 6-(2-hydroxy-3-iodobenzylamino)purine mesylate, 6-(2-hydroxy-5-iodobenzylamino)purine mesylate, 6-(4-hydroxy-5-iodobenzylamino)purine mesylate, 6-(3-hydroxy-5-iodobenzylamino)purine mesylate, 6-(2-hydroxy bromobenzylamino)purine mesylate, 6-(4-hydroxy-3-bromobenzylamino)purine mesylate, 6-(3-hydroxy-5-bromobenzylamino)purine mesylate, 6-(2-hydroxy-3-fluorobenzylamino)purine mesylate, 6-(2-hydroxy-5-fluorobenzylamino)purine mesylate, 6-(4-hydroxy-3-fluorobenzylamino)purine mesylate, 6-(3-hydroxy-5-fluorobenzylamino)purine mesylate, 6-(2,3-dihydroxy methoxybenzylamino)purine mesylate, 6-(2,4-dihydroxy-3-methoxybenzylamino)purine mesylate, 6-(2,5-dihydroxy-4-methoxybenzylamino)purine mesylate, 6-(2-hydroxybenzylamino)purine mesylate, 6-(3-hydroxybenzylamino)purine mesylate, 6-(3-hydroxy-4-methoxybenzylamino)purine mesylate, 6-(3-hydroxy-5-methoxybenzylamino)purine mesylate, 6-(2-hydroxy-3-methoxybenzylamino)purine mesylate, 6-(4-hydroxy-3-methoxybenzylamino)purine mesylate, 6-(2-hydroxy-4-methoxybenzylamino)purine mesylate, 6-(4-hydroxy-2-methoxybenzylamino)purine mesylate, 6-(2-methoxybenzylamino)purine mesylate, 6-(3-methoxybenzylamino)purine mesylate, 6-(4-methoxybenzylamino)purine mesylate, 6-(2,3-dimethoxybenzylamino)purine mesylate, 6-(2,4-dimethoxybenzylamino)purine mesylate, 6-(2,5-dimethoxybenzylamino)purine mesylate, 6-(3,4-dimethoxybenzylamino)purine mesylate, 6-(2,3,4-trimethoxybenzylamino)purine mesylate, 6-(2,3,5-trimethoxybenzylamino)purine mesylate, 6-(3,5-dimethyl-4-hydroxybenzylamino)purine mesylate, 6-allylaminopurine mesylate, 6-isopentenylaminopurine mesylate, 6-(3,3-dimethylallylamino)purine mesylate, 6-(3-hydroxymethyl-3-methylallyl)amino)purine mesylate, 6-(Z)-(4-hydroxy-3-methylbut-2-en-1-ylamino)purine mesylate, 6-(E)-(4-hydroxy-3-methylbut-2-en-1-ylamino) purine mesylate, 6-(Z)-(1'-methyl-4-hydroxy-3-methylbut-2-en-1-ylamino)purine mesylate, 6-(E)-(1'-methyl-4-hydroxy-3-methylbut-2-en-1-ylamino)purine mesylate, 6-(4-hydroxy-3-methylbutylamino)purine mesylate, and 6-(1'-methyl-4-hydroxy-3-methylbutylamino)purine mesylate.

Particularly preferred are the heterocyclic cytokinin mesylate salts of the general formula I selected from the group comprising 6-furfurylaminopurine mesylate, 6-(2-chlorobenzylamino)purine mesylate, 6-(3-chlorobenzylamino)purine mesylate, 6-(2-fluorobenzylamino)purine mesylate, 6-(3-fluorobenzylamino)purine mesylate, 6-(4-fluorobenzylamino)purine mesylate, 6-(2-hydroxybenzylamino)purine mesylate, 6-(3-hydroxybenzylamino)purine mesylate, 6-(2-methoxybenzylamino)purine mesylate, 6-(3-methoxybenzylamino)purine mesylate, 6-(3-methylbut-2-en-1-ylamino)purine mesylate, 6-benzylaminopurine mesylate, 6-(4-hydroxy-3-methylbut-2-en-1-ylamino)purine mesylate, 6-(Z)-(4-hydroxy-3-methylbut-2-en-1-ylamino) purine mesylate t, 6-(E)-(4-hydroxy-3-methylbut-2-en-1-ylamino)purine mesylate, 6-(Z)-(4-hydroxy-1,3-dimethylbut-2-en-1-ylamino)purine mesylate, 6-(E)-(4-hydroxy-1,3-dimethylbut-2-en-1-ylamino)purine mesylate, 6-(4-hydroxy-3-methylbutylamino)purine mesylate, and 6-(4-hydroxy-1,3-dimethylbutylamino)purine mesylate.

In one aspect, the object of the present invention are also crystalline cytokinin mesylate salts of the general formula I.

Preferably, the invention provides crystalline benzylaminopurine mesylate having characteristic peaks in an X-ray powder diffraction spectrum measured using CuKα radiation: 6.2; 10.0; 15.2; 5,7; 18.6; 18,8; 19.3; 20.4; 23.5; 23.8; 24.4; 27.6±0.2° 2-theta.

Preferably, the invention provides crystalline meta-topolin mesylate ((3-hydroxybenzylamino)purine mesylate) having characteristic peaks in an X-ray powder diffraction spectrum measured using CuKα radiation: 8.1; 9.7; 13.1; 15.6; 16.8; 17.6; 19.1; 19.5; 22.2; 24.6; 24.8; 24.9; 25.7±0.2° 2-theta.

Preferably, the invention provides crystalline ortho-topolin mesylate ((2-hydroxybenzylamino)purine mesylate) having characteristic peaks in an X-ray powder diffraction spectrum measured using CuKα radiation: 9.8; 12.1; 16.8; 17.8; 18.3; 18.3; 20.7; 23.3; 24.1; 25.1; 26.8±0.2° 2-theta.

Preferably, the invention provides crystalline kinetin mesylate (6-furfurylaminopurine mesylate) having characteristic peaks in an X-ray powder diffraction spectrum measured using CuKα radiation: 6.2; 18.9; 19.8; 20.4; 22.6; 23.9; 27.7; 27.8±0.2° 2-theta.

The mesylate salts of formula I are generally obtained by reacting a base (N6-substituted adenine derivative) and methylsulfonic acid in a polar solvent, especially in C1-C4 alcohol, most preferably in methanol. The crystallization is then preferably carried out from acetone.

The purine cytokinin mesylate salts of general formula I, and in particular their crystalline forms, have improved physicochemical properties, in particular better solubility in polar solvents including water, higher stability and bioavailability, and easier industrial-scale production of these substances.

The cytokinin mesylate salts of general formula I have a wide range of biological activities, including antioxidant, anti-senescent, supporting floem loading, shoot and root forming control, and pro-differentiation activities, which are especially useful in agricultural and biotechnological applications (e.g. in plant tissues and cells). Their great advantage, which also increases their biological activities, is increased water solubility and bioavailability. The compounds of the present invention (and formulations containing the compounds) have minimal or no toxicity. This enables their use in a wide range of applications.

The invention relates to the use of compounds of general formula I for the protection of plant cells in vivo and in vitro against oxidative and electrophilic stress.

The invention also relates to the use of the compounds of general formula I as antioxidants for inhibiting lipid, protein and DNA peroxidation in plants in vivo and in vitro.

The present invention further relates to the use of cytokinin mesylates of general formula I for increasing yield, improving rooting, increasing the number of shoots, increasing of multiplication and delaying senescence in the production of useful plants and agricultural crops, in particular cereals (wheat, barley, rice, maize, rye, oat, sorghum, and related species), beet (sugar beet and fodded beet); pomes, drupes and soft fruits (apples, pears, plums, peaches, almonds, cherries, strawberries and blackberries); leguminous plants (beans, lentils, peas, soybeans); oil plants (rape, mustard, poppy, olives, sunflowers, coconut, *Ricinus*, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, cinnamomum, camphor) or plants such as tobacco, nuts, eggplants, sugar cane, tea, vine grapes, hops, bananas and natural rubber and medicinal plants, as well as ornamentals. Crops include those which have been rendered tolerant towards classes of growth factors by conventional breeding methods or genetic engineering methods.

The present invention also relates to the use of cytokinin mesylate salts of general formula I as growth and pro-differentiation factors, in particular for plants. They can be used for optimization of conditions in plant tissue cultures in vitro. In particular, in vitro conditions cover somatic embryogenesis, micropropagation, androgenesis, gynogenesis, suspension and protoplast cultures. The compounds according to the present invention may also be used as inhibitors of root formation in plant tissue cultures.

The cytokinin mesylates of general formula I can further be used according to the present invention in plant tissue cultures to suppress undesirable physiological disorders such as hyperhydricity, shoot tip necrosis, chimera formation, inhibition of root formation during acclimatization and premature senescence.

The present invention relates to the use of the compounds of general formula I as growth regulators in plant tissue cultures for stimulating proliferation and morphogenesis.

The invention also relates to the use of the compounds of general formula I as growth regulators in the cloning of plant and animal germ cells and embryos, preferably oocytes.

The invention also relates to the use of the compounds of general formula I for inhibiting or delaying the senescence of plant cells and plants.

The cytokinin mesylate salts of general formula I can also be used in agriculture and biotechnology for inhibition, delaying, or reducing the adverse effects of senescence, in vivo and in vitro; the uses also include improving the overall appearance and condition of the plants, in particular plant epidermal and mesophyll cells, and also for inhibition, delay or reduction of senescence, yellowing, chloroplast loss and/or chlorophyll loss.

This invention further provides use of the compounds of general formula I for rejuvenation of plant cells and/or stimulation of cell proliferation and/or cell differentiation in an organism.

The above uses of the compounds of general formula I usually involve the application of an effective amount of at least one compound of general formula I to cells (e.g. in tissue culture), plant organelles, parts of plants or plants. The compounds of general formula I can be administered alone or—more usually—in the form of preparations with solvents, carriers and/or auxiliaries.

The present invention further provides agricultural and/or biotechnological compositions comprising at least one cytokinin mesylate salt of general formula I, and an acceptable carrier and/or solvent. The compounds of general formula I are used in unmodified form or, preferably, together with excipients conventionally employed in the art of preparations. To this end they are conveniently formulated as concentrates of active compounds as well as suspensions and dispersions, preferentially isotonic water solutions, suspensions and dispersion, diluted emulsions, soluble powders, dusts, granulates, creams, gels, oil suspensions and also encapsulations, e.g. polymeric substances. As with the type of the preparation, the methods of application, such as spraying, atomizing, dusting, scattering, coating or pouring, are chosen in accordance with the intended objectives and the prevailing circumstances. The preparations may be sterilized and/or contain further excipients of neutral nature such as preservatives, stabilizers, wetting agents or emulgators, solubilizing agents, as well as fertilizers, micronutrient donors or other formulations for obtaining special effects.

The cytokinin mesylate salts of the general formula I can be mixed with other growth regulators and pesticides, resulting in synergistic activities.

As used herein, the term in vivo means use in a living plant or in a part of a plant capable of independent living. The term in vitro means use in a cell, in an organelle, or in a harvested part of a plant, or in an embodiment comprising only functional compounds from plants or animals, such as enzymes or information transfer agents in the cell.

PREPARATIONS

Preparations comprising a compound of general formula I (active ingredient) and, where appropriate, one or more solid or liquid auxiliaries (excipients), are prepared in a known manner, e.g. by mixing and/or grinding the active ingredients with the excipients, e.g. solvents or solid carriers. In addition, surface-active compounds (surfactants) may also be used in the preparations.

Depending on the nature of the compound of general formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485.

Also suitable in the preparation of the compositions containg compound of general formula I according to the invention are the surfactants conventionally used in formulation technology, which are described, *inter alia*, in "McCutcheon's Detergents and Emulsifiers Annual" MC Publishing Corp., Ridgewood N.J., 1981; Stache, H., "Tensid-Taschenbuch", Carl Hanser Verlag, Munich, 1981; and M. and J.Ash, "Encyclopedia of Surfactants", Vol. 1-3, Chemical Publishing Co., New York, 1980-81. The formulation of the preparation usually contains from 0.1 to 99%, especially 0.1 to 95% (w/w) of active ingredient of cytokinin mesylate and from 0.1 to 25% by weight of a surfactant.

While commercial products are usually formulated as concentrates, the end user will normally employ diluted formulations. The compositions may also comprise further ingredients, such as stabilisers, e.g. vegetable oils or epoxidised vegetable oils (epoxidised palm oil, rapeseed oil or soybean oil), antifoams, e.g. silicone oil, preservatives, stabilizers, wetting agents or emulsifiers, viscosity factors, binders, tackifiers, and also fertilisers or other active ingredients. Preferred formulations have especially the following compositions: (%=percent by weight).

Emulsifiable Concentrates:

active ingredient: 1 to 90%, preferably 5 to 20%
surfactant: 1 to 30%, preferably 10 to 20%
liquid carrier: 5 to 94%, preferably 70 to 85%

Dusts:
- active ingredient: 0.1 to 10%, preferably 0.1 to 5%
- solid carrier: 99.9 to 90%, preferably 99.9 to 95%

Suspension Concentrates:
- active ingredient: 5 to 75%, preferably 10 to 50%
- water: 94 to 24%, preferably 88 to 30%
- surfactant: 1 to 40%, preferably 2 to 30%

Wettable Powders:
- active ingredient: 0.5 to 90%, preferably 1 to 80%
- surfactant: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.9 to 70%, preferably 99.9 to 85%

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of the compounds of general formula I, or of compositions comprising these compounds, various methods and techniques come into consideration, such as, for example, the following:

i) Seed Dressing
- a) Dressing of the seeds with a wettable powder formulation of a compound of the general formula I by shaking in a vessel until uniformly distributed over the seed surface (dry dressing). In that procedure approximately from 1 to 500 g of compound of the general formula I (4 g to 2 kg of wettable powder) are used per 100 kg of seed.
- b) Dressing of the seeds with an emulsifiable concentrate of a compound of formula I according to method a) (wet dressing).
- c) Dressing by immersing the seeds for 1 to 72 hours in a liquid comprising from 100 to 1000 ppm of a compound of general formula I and preferably subsequently drying the seeds (immersion dressing). Dressing the seeds or treating the germinated seedlings are naturally the preferred methods of application, because treatment with the active ingredients is directed entirely at the target crop. Generally from 1 to 1000 g of the active ingredient, preferably from 5 to 250 g of the active ingredient, are used per 100 kg of seed, but depending on the methodology, which also enables the addition of other active ingredients or micronutrients: the concentration limits indicated can be varied up or down (repeat dressing).

ii) Application as a Tank Mixture by Spraying.

A liquid formulation of the active ingredient, optionally together with another growth regulator is sprayed to the plants, the rate of application of the active ingredient being from 0.05 to 0.5 kg per hectare. Such tank mixtures are applied before or after sowing, in particular to emerged plants (foliar application) in the amount of the liquid preparation of 100-600 l/ha, depending on the crop.

iii) Application to the Seed Furrow

The compounds of formula I are introduced into an open, sown seed furrow in the form of an emulsifiable concentrate, wettable powder or granules. Once the seed furrow has been covered over, the growth regulator is applied in the usual manner in the pre-emergence process.

iv) Controlled Release of Active Ingredients

The compound(s) of formula I are applied in solution to mineral granule carriers or polymerised granules (urea/formaldehyde) and dried. If desired, it a coating may be applied that allows the active ingredient to be released in metered amounts over a specific period of time (coated granules).

EXAMPLES

Figure 1:
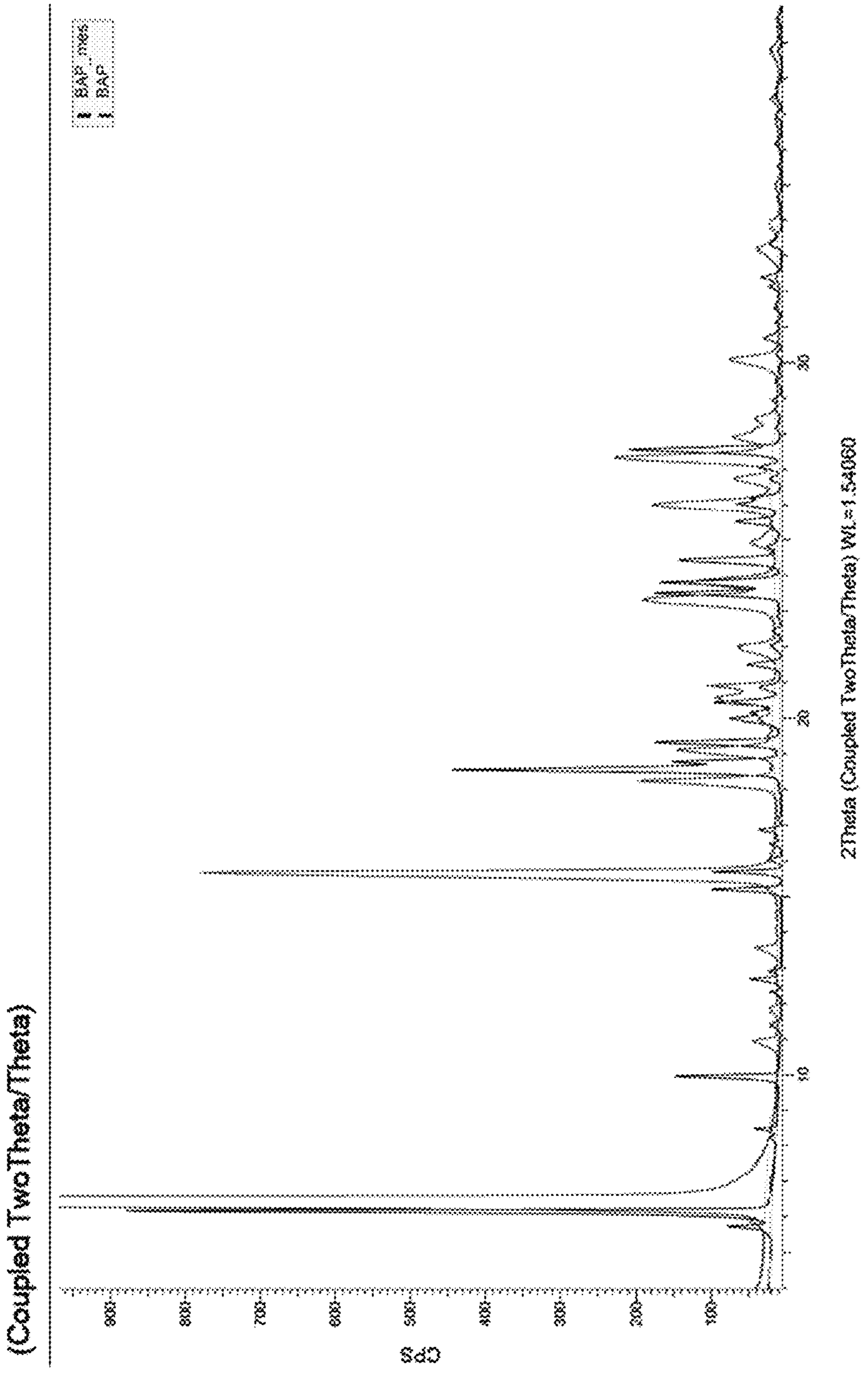
FIG. 1 shows comparison of XRPD patterns of BAP mesylate crystalline salt and BAP.

The following examples serve to illustrate the invention without limiting the scope thereof. Unless otherwise stated, all percentages and the like amounts are based on weight.

Example 1: Preparation of Crystalline Meta-Topolin [6-(3-Hydroxybenzylamino)Purine] Mesylate 6-(3-hydroxybenzylamino)purine (meta-topolin free base, 241 mg; 1 mmol) was suspended in stirred methanol (10 ml) at room temperature and methanesulphonic acid (100 mg; 1.03 mmol) was added. After a short time, the suspension changed into clear yelllowish solution. The resulting reaction mixture was stirred at room temperature for 20 minutes and then evaporated on rotary vacuum evaporator to yellowish solid residue which was treated with heptane (10 ml) to obtain yellowish crystalline powder. The product was filtered off, washed with heptane (3×5 ml) and dried at 60° C. to constant weight. Yield: 88%; purity (HPLC-UV/VIS): 98%+; ESI-MS: $[M+H]^+$=338.5

Translucent white crystals suitable for X-ray single crystal and XRPD diffraction were prepared by the dissolution of the solid substance in methanol by 7-days free evaporation of the solvent.

Example 2: Preparation of Crystalline Ortho-Topolin [6-(2-Hydroxybenzylamino)Purine] Mesylate 6-(2-hydroxybenzylamino)purine (ortho-topolin free base, 241 mg, 1 mmol) was suspended in stirred methanol (15 ml) at room temperature and methanesulphonic acid (100 mg, 1.03 mmol) was added. The resulting mixture was stirred at room temperature for 30 minutes and then evaporated on rotary vacuum evaporator to white solid residue which was treated with hexane (10 ml) to obtain white crystalline powder. The product was filtered off, washed with hexane (3×5 ml) and dried at 60° C. to constant weight. Yield: 310 mg (92%); purity (HPLC-UV/VIS): 99%+; ESI-MS: $[M+H]^+$=338.51. Translucent white needle like crystals suitable for X-ray single crystal as well as XRPD diffraction were prepared by the dissolution of the solid substance in methanol by 7-days free evaporation of the solvent.

Example 3: Preparation of Crystalline 6-Benzylaminopurine (BAP) Mesylate 500 mg of 6-benzylaminopurine was disolved in 50 ml of methanol under 50° C. for 30 min. After 6-benzylaminopurine was completely disolved, 144 μl of methanesulfonic acid was added drop by drop. Solution went under reflux for 1 hour. After that the solution was cooled to RT and poured into beaker, covered with parafilm. Solution was put in the fridge for crystallization for 7 days. Crystals were then filtered and washed off with methanol. Yield: 86%, purity (HPLC-UV/VIS): 98%, ESI-MS: $[M+H]^+$=322.11 Small white crystals suitable for XRPD diffraction were prepared by the dissolution of the solid substance in methanol by 7-days at at 7° C.

Example 4: Preparation of Crystalline 6-Furfuryladenine (Kinetin) Mesylate 500 mg of 6-furfuryladenine was disolved in 50 ml of methanol under 50° C. for 30 min. After 6-furfuryladenine was completely disolved, 158 μl of methanesulfonic acid was added drop by drop. Solution went under reflux for 1 hour. After that the solution was cooled to RT and poured into beaker, covered with parafilm. Solution was put in the fridge for crystallization for 7 days. Crystals were then filtered and washed off with methanol. Yield: 85%, purity (HPLC-UV/VIS): 98%, ESI-MS: $[M+H]^+$=312.11 Small translucent crystals suitable for XRPD diffraction were prepared by the dissolution of the solid substance in methanol by 6-days at at 7° C.

Example 5: Preparation of Crystalline (E)-Zeatin (Trans-Zeatin) Mesylate ((E)-4-(9H-Purin-6-Ylamino)-2-Methybut-2-En-1-ol)Methanesulphonate)

(E)-zeatin (219 mg, 1 mmol) was dissolved in methanol (25 ml) and methasulfonic acid (100 mg, 1.03 mmol) was added dropwise. The solution was mixed 20 min at laboratory temperature a afterwards concentrated and evaporated on rotary vacuum evaporator to white-yellowish solid residue which was treated with acetone (10 ml) at laboratory temperature. White crystalline product was filtrated off, washed with acetone (3×5 ml) and dried into constant weight. Yield: 255 mg, 81%, purity (HPLC-UV/VIS): 98%, ESI-MS: $[M+H]^+$=220.11.

Example 6: Preparation of Crystalline (Z)-Zeatin (Cis-Zeatin) Mesylate ((Z)-4-((9H-Purin Ylamino)-2-Methylbut-2-En-1-ol) Methanesulphonate)

Prepared identically as previous (E)-isomer (go to example 5). Yield: 240 mg; 76%). Purity (HPLC-UV/VIS): 98%+, ESI-MS: $[M+H]^+$=220.11

Example 7: Preparation of Crystalline RS-(+/−)-Dihydrozeatin Mesylate ((RS)-4-((9H-Purin Ylamino)-2-Methylbutan-1-ol) Methanesulphonate)

RS-(+/−)-dihydrozeatin (221 mg; 1 mmol) was dissolved in methanol (20 ml) and methanesulphonic acid was added dropwise to the solution (100 mg; 1.03 mmol). Solution was mixed for 30 min under laboratory temperature and then concentrated and evaporated on rotary vacuum evaporator to almost white solid that was mixed with acetone (10 ml) under laboratory temperature. White crystalline solid was filtrated off, washed with acetone (3×5 ml) and diethylester (2×5 ml) and dried up to constant weight. Yield: 260 mg (82%). Purity (HPLC-UV/VIS): 98%+, ESI-MS: $[M+H]^+$=222.13

Example 8: Preparation of Crystalline Isopentenyladenine Mesylate (N-3-(Methylbut-2-En-1-Yl)-9H-Purin-6-Amin Methanesulphonate)

Isopentenyladenine (203 mg; 1 mmol) was dissolved in methanol (25 ml) and methanesulphonic acid was added dropwise (100 mg; 1.03 mmol) to the solution. Solution was mixed for 30 min under laboratory temperature and concentrated and evaporated at rotary vacuum evaporator to white solid that was washed with acetone (10 ml) under laboratory temperature. White crystalline product was filtrated off, washed with acetone (3×5 ml) and dried to constant weight. Yield: 257 mg (86%). Purity (HPLC-UV/VIS): 99%+, ESI-MS: $[M+H]^+$=204.12

Example 9: X-Ray Powder Diffraction (XRPD) of Crystalline Salts of BAP Mesylate, Meta-Topolin Mesylate, Ortho-Topolin Mesylate and Kinetin Mesylate and Comparison of their Difractograms with XRPD Patterns of BAP, Meta-Topolin, Ortho-Topolin and Kinetin X-ray powder diffraction (XRPD): X-ray powder diffraction studies were performed on a Bruker D8 Advance ECO diffractometer with Cu K-alpha radiation and SSD160 detector. Approximately 5 mg of sample was gently compressed on the XRPD sample holder. The sample was then loaded into a Bruker D8-Discover diffractometer in transmission mode and analyzed using the experimental conditions shown below.

XRPD Measurement Conditions

| Scan axis gonio | |
|---|---|
| Start position [°2th.] | 4.0000 |
| End position [°2th.] | 40.00 |
| Step size [°2th.] | 0.0100 |
| Scan step time [s] | 0.3 (48) s |
| Scan type | continuous |
| Offset [°2th.] | 0.0000 |
| Divergence slit type | fixed |
| Divergence slit size [°] | 0.3000 |
| Specimen length [mm] | 10.00 |
| Receiving slit size [mm] | — |
| Measurement temperature [° c.] | 25.00 |
| Anode material | Cu |
| K-alpha1 [å] | 1.54060 |
| K-alpha2 [å] | 1.54443 |
| K-beta [å] | 1.39225 |
| K-a2/k-a1 ratio | 0.50000 |
| Generator settings | 40 ma, 25 kv |
| Diffractometer number | 0 |
| Goniometer radius [mm] | 250.00 |
| Dist. Focus-diverg. Slit [mm] | 110.00 |
| Ni Kbeta filter | yes |
| Incident beam monochromator | no |
| Spinning | no |

Figure 2:
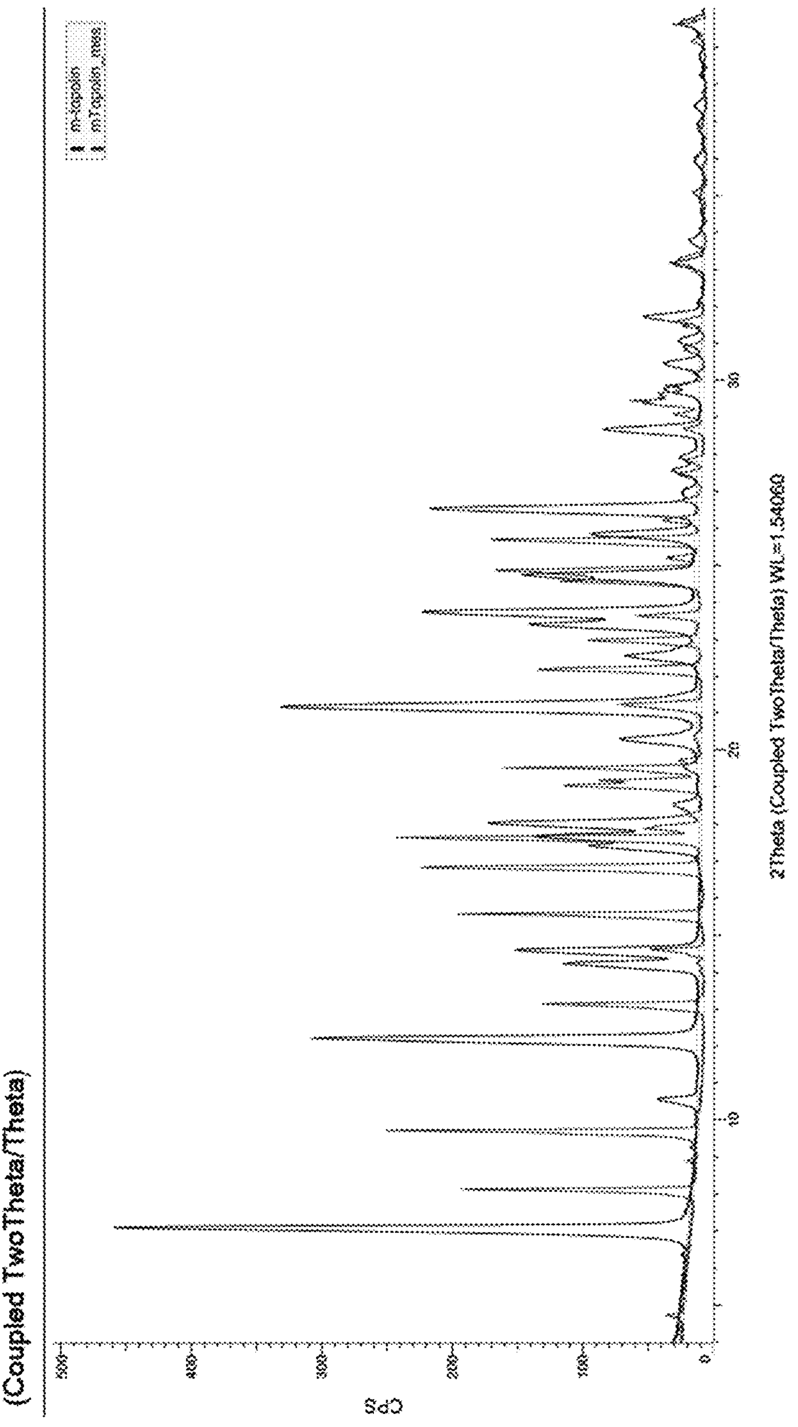
FIG. 2 shows comparison of XRPD patterns of meta-topolin mesylate crystalline salt and meta-topolin.
Figure 3:
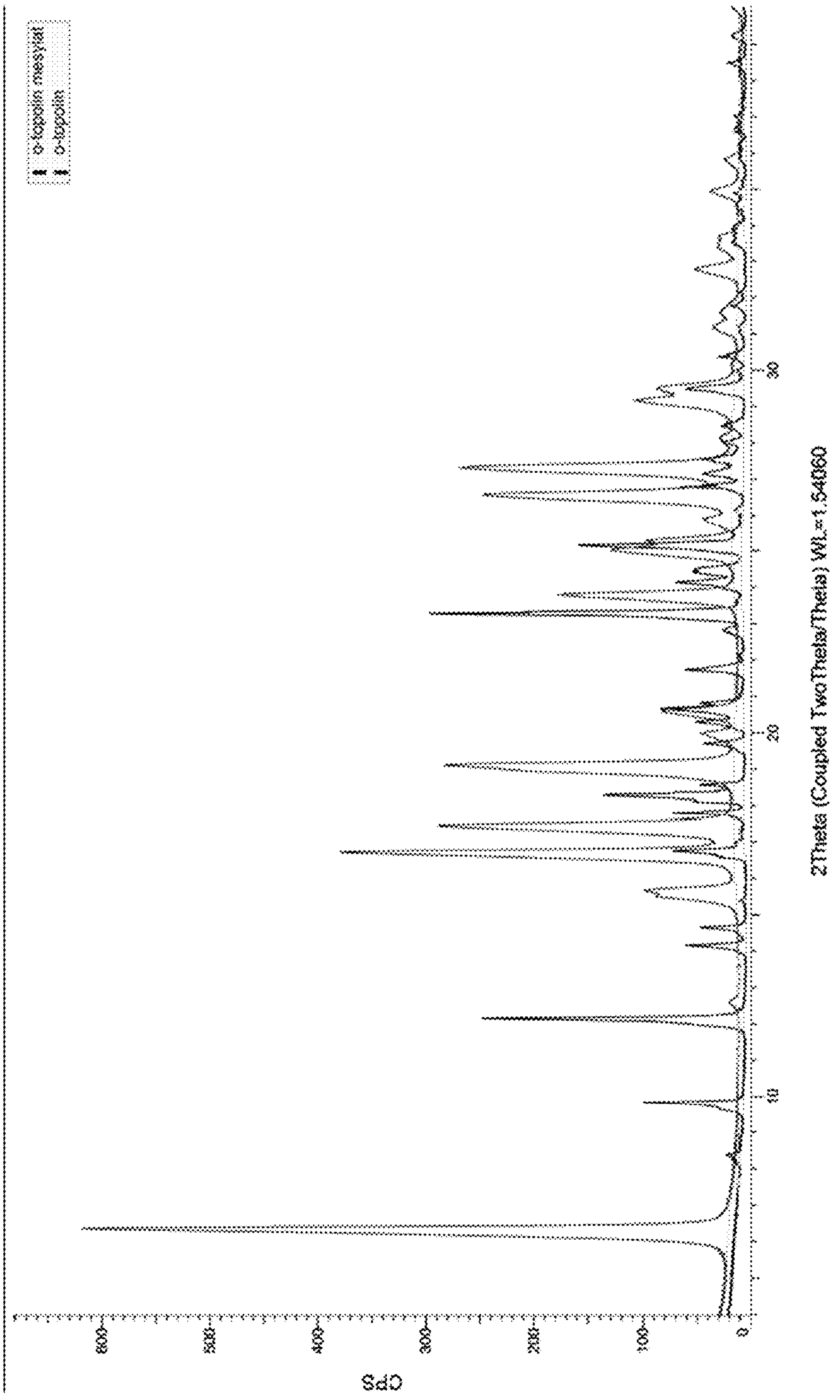
FIG. 3 shows comparison of XRPD patterns of ortho-topolin crystalline salt and ortho-topolin.
Figure 4:
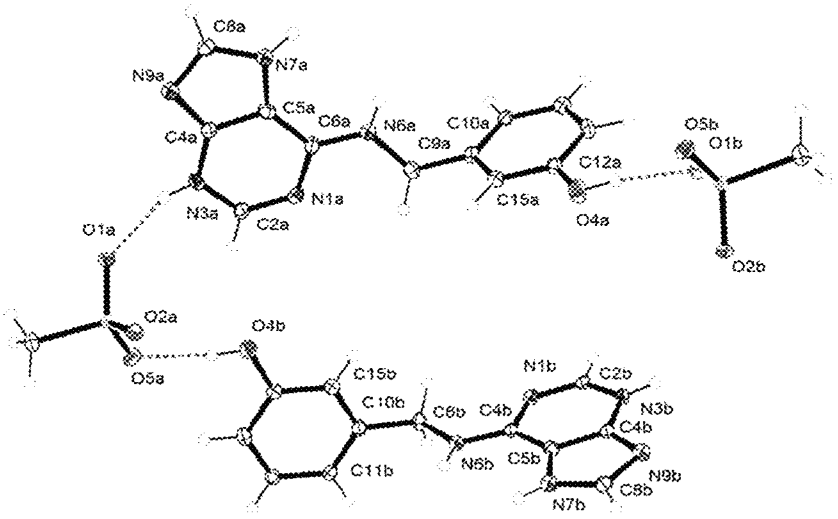
FIG. 4 shows molecular structure of meta-topolin mesylate crystalline salt including intermolecular hydrogen bond network obtained by single crystal X-ray diffraction.

The comparison of XRPD patterns for BAP mesylate and BAP is shown in FIG. 1 while the peaks detected for BAP mesylate are given in Table 1. The peaks for free base BAP are given in Table 2. The comparison of meta-topolin mesylate crystalline salt and meta-topolin. XRPD patterns is shown in FIG. 2. The peaks detected for meta-topolin mesylate are given in Table 3 while the peaks for meta-topolin free base are given in Table 4. The comparison of XRPD patterns of ortho-topolin mesylate crystalline salt and ortho-topolin is shown in FIG. 3 and the comparison of XRPD pattern of kinetin mesylate crystalline salt and kinetin is shown in FIG. 4, The XRPD peaks for ortho-topolin mesylate are given in Table 5, while for ortho-topolin in Table 6. The XRPD peaks for kinetin mesylate are given in Table 7 and for kinetin free base in Table 8. As apparent, the patterns of crystalline mesylate salts at FIGS. 1, 2, 3 and 4 significantly differ from the XRPD patterns of original bases, and all the materials including free bases used for the comparison are crystalline.

TABLE 1

Relative intenstities of diffracted radiation, measured angles, d-spacing obtained by XRPD for BAP mesylate crystalline salt

| Angle | d--spacing | Rel. Intensity |
|---|---|---|
| 5.721 | 15.43427 | 6.9% |
| 6.155 | 14.34703 | 100.0% |
| 8.216 | 10.75322 | 1.0% |
| 8.453 | 10.45186 | 3.5% |
| 9.961 | 8.87309 | 17.5% |
| 11.405 | 7.75224 | 1.3% |
| 12.331 | 7.17224 | 1.6% |
| 12.68 | 6.97581 | 5.1% |
| 12.908 | 6.85299 | 2.0% |
| 14.62 | 6.05411 | 0.4% |
| 15.205 | 5.82247 | 11.9% |
| 15.698 | 5.64048 | 11.8% |
| 16.037 | 5.5221 | 2.3% |
| 16.472 | 5.37725 | 1.6% |
| 16.681 | 5.31033 | 0.9% |
| 16.872 | 5.25081 | 3.8% |
| 17.214 | 5.14723 | 0.8% |
| 17.683 | 5.01177 | 0.3% |
| 18.035 | 4.91453 | 0.2% |
| 18.557 | 4.7775 | 55.5% |
| 18.764 | 4.72538 | 17.3% |
| 19.319 | 4.59075 | 21.4% |
| 19.986 | 4.43908 | 8.1% |
| 20.139 | 4.4056 | 4.7% |
| 20.448 | 4.33983 | 11.3% |
| 20.868 | 4.25336 | 3.4% |
| 21.508 | 4.12834 | 5.7% |
| 22.022 | 4.03299 | 1.4% |
| 22.449 | 3.95727 | 1.3% |
| 22.85 | 3.8887 | 0.6% |
| 23.055 | 3.85465 | 0.2% |
| 23.5 | 3.78255 | 21.4% |
| 23.805 | 3.73478 | 20.5% |
| 24.427 | 3.6411 | 17.4% |
| 24.807 | 3.58623 | 2.1% |
| 24.973 | 3.56275 | 0.5% |
| 25.33 | 3.51335 | 0.9% |
| 25.519 | 3.48779 | 7.8% |
| 26.035 | 3.41984 | 7.3% |
| 26.174 | 3.40192 | 4.6% |
| 26.749 | 3.33008 | 1.3% |
| 27.077 | 3.29052 | 3.2% |
| 27.558 | 3.23414 | 25.5% |
| 28.193 | 3.16277 | 0.7% |
| 28.69 | 3.1091 | 1.2% |
| 28.949 | 3.08183 | 1.5% |
| 29.474 | 3.02815 | 1.0% |
| 29.782 | 2.99751 | 0.3% |
| 29.838 | 2.992 | 0.3% |
| 30.234 | 2.95367 | 0.8% |
| 30.69 | 2.91085 | 2.9% |
| 31.133 | 2.87043 | 0.9% |
| 31.55 | 2.83341 | 1.2% |
| 31.852 | 2.80728 | 0.4% |
| 32.137 | 2.78299 | 2.1% |
| 32.388 | 2.76198 | 3.4% |
| 33.356 | 2.68404 | 2.2% |
| 33.503 | 2.67258 | 1.1% |

TABLE 1-continued

Relative intenstities of diffracted radiation, measured angles, d-spacing obtained by XRPD for BAP mesylate crystalline salt

| Angle | d--spacing | Rel. Intensity |
|---|---|---|
| 34.184 | 2.62088 | 0.3% |
| 34.666 | 2.58558 | 0.8% |
| 35.559 | 2.52264 | 0.8% |
| 36.197 | 2.47962 | 1.1% |
| 36.583 | 2.45432 | 0.2% |
| 36.947 | 2.43102 | 0.9% |
| 37.494 | 2.39679 | 0.9% |
| 37.754 | 2.38088 | 0.9% |
| 38.059 | 2.36248 | 0.2% |
| 38.77 | 2.32077 | 0.6% |
| 39.185 | 2.29713 | 0.3% |
| 39.679 | 2.26968 | 0.9% |

TABLE 2

Relative intenstities of diffracted radiation, measured angles, d-spacing obtained by XRPD for BAP

| Angle | d spacing | Rel. Intensity |
|---|---|---|
| 5.831 | 15.14553 | 0.3% |
| 6.448 | 13.69776 | 100.0% |
| 10.915 | 8.09952 | 0.6% |
| 11.793 | 7.49808 | 0.2% |
| 12.925 | 6.8441 | 0.1% |
| 13.512 | 6.54808 | 0.5% |
| 15.623 | 5.66738 | 11.7% |
| 17.209 | 5.14865 | 0.0% |
| 18.198 | 4.87094 | 2.3% |
| 19.068 | 4.65074 | 2.2% |
| 19.429 | 4.56515 | 0.1% |
| 19.951 | 4.44672 | 0.3% |
| 20.532 | 4.32216 | 1.3% |
| 20.844 | 4.25832 | 0.9% |
| 21.952 | 4.04573 | 0.8% |
| 23.292 | 3.81593 | 2.7% |
| 23.789 | 3.73726 | 1.9% |
| 24.89 | 3.57441 | 0.5% |
| 25.067 | 3.54962 | 0.2% |
| 25.985 | 3.42626 | 2.5% |
| 26.73 | 3.33245 | 0.9% |
| 27.312 | 3.26272 | 3.6% |
| 27.878 | 3.19774 | 0.8% |
| 28.408 | 3.13926 | 0.4% |
| 30.068 | 2.96962 | 1.0% |
| 31.591 | 2.8299 | 0.0% |
| 32.359 | 2.76439 | 0.1% |
| 33.177 | 2.6981 | 0.5% |
| 33.867 | 2.64472 | 0.2% |
| 34.606 | 2.58989 | 0.0% |
| 34.978 | 2.56322 | 0.1% |
| 36.63 | 2.45128 | 0.0% |
| 36.856 | 2.4368 | 0.0% |
| 37.421 | 2.40128 | 0.1% |
| 37.819 | 2.37693 | 0.0% |
| 38.447 | 2.33951 | 0.0% |
| 38.777 | 2.32039 | 0.1% |
| 39.762 | 2.26515 | 0.0% |

TABLE 3

Relative intenstities of diffracted radiation, measured angles, d-spacing obtained by XRPD for meta-topolin mesylate (m-topolin mes)

| Angle | d spacing | Rel. Intensity |
|---|---|---|
| 4.708 | 18.75442 | 4.1% |
| 8.107 | 10.89665 | 67.3% |
| 8.872 | 9.95929 | 2.9% |
| 9.295 | 9.5067 | 2.0% |
| 9.683 | 9.12666 | 78.1% |
| 10.077 | 8.77112 | 0.7% |
| 13.118 | 6.74372 | 46.6% |
| 14.081 | 6.28446 | 1.1% |
| 14.26 | 6.20607 | 2.0% |
| 14.589 | 6.06695 | 15.9% |
| 15.55 | 5.6941 | 63.7% |
| 16.821 | 5.26641 | 100.0% |
| 17.614 | 5.03108 | 98.6% |
| 17.896 | 4.9525 | 18.9% |
| 18.234 | 4.86135 | 4.3% |
| 19.066 | 4.6511 | 43.0% |
| 19.17 | 4.62614 | 36.0% |
| 19.405 | 4.57075 | 20.8% |
| 19.466 | 4.55634 | 31.6% |
| 19.508 | 4.54665 | 67.9% |
| 19.554 | 4.53623 | 33.9% |
| 19.685 | 4.50619 | 6.9% |
| 20.343 | 4.36194 | 2.4% |
| 21.195 | 4.1885 | 26.7% |
| 22.198 | 4.00154 | 58.1% |
| 22.97 | 3.86865 | 39.2% |
| 23.64 | 3.76049 | 21.9% |
| 24.576 | 3.61945 | 51.3% |
| 24.785 | 3.58936 | 57.8% |
| 24.862 | 3.57834 | 72.9% |
| 25.198 | 3.53144 | 9.8% |
| 25.673 | 3.46723 | 69.1% |
| 26.227 | 3.39523 | 12.7% |
| 26.754 | 3.32944 | 6.5% |
| 27.512 | 3.23941 | 7.0% |
| 27.455 | 3.24599 | 8.3% |
| 27.833 | 3.20287 | 6.1% |
| 28.679 | 3.1102 | 6.7% |
| 29.083 | 3.06798 | 10.5% |
| 29.423 | 3.03326 | 19.7% |
| 29.57 | 3.01855 | 14.6% |
| 29.799 | 2.9958 | 9.4% |
| 30.172 | 2.95961 | 3.7% |
| 30.861 | 2.89509 | 6.1% |
| 31.554 | 2.83313 | 7.7% |
| 32.193 | 2.77827 | 1.9% |
| 32.495 | 2.75319 | 1.0% |
| 33.01 | 2.7114 | 3.1% |
| 33.24 | 2.69315 | 9.1% |
| 34.109 | 2.62647 | 1.7% |
| 34.52 | 2.59613 | 0.7% |
| 35.075 | 2.55631 | 4.9% |
| 35.718 | 2.51178 | 1.3% |
| 36.412 | 2.46549 | 1.4% |
| 36.776 | 2.44189 | 2.4% |
| 37.815 | 2.37715 | 1.0% |
| 38.246 | 2.35137 | 1.8% |
| 38.611 | 2.32997 | 0.5% |
| 39.182 | 2.29732 | 5.0% |
| 39.606 | 2.27371 | 9.3% |
| 39.728 | 2.267 | 4.8% |

TABLE 4

Relative intenstities of diffracted radiation, measured angles, d-spacing obtained by XRPD for meta-topolin

| Angle | d spacing | Rel.. Intensity |
|---|---|---|
| 7.074 | 12.48654 | 100.00% |
| 10.535 | 8.39088 | 7.00% |
| 12.208 | 7.24412 | 67.80% |
| 14.224 | 6.22163 | 24.20% |
| 14.583 | 6.06943 | 32.50% |
| 17.44 | 5.08094 | 19.30% |
| 17.656 | 5.01919 | 29.80% |
| 18.011 | 4.92124 | 38.00% |
| 18.513 | 4.78881 | 4.50% |
| 19.534 | 4.54079 | 2.50% |
| 20.278 | 4.37586 | 13.70% |
| 21.16 | 4.19532 | 77.10% |
| 22.552 | 3.93939 | 12.90% |
| 23.403 | 3.79813 | 30.30% |
| 23.729 | 3.74668 | 49.90% |
| 24.726 | 3.59781 | 30.70% |
| 25.839 | 3.44522 | 19.00% |
| 26.523 | 3.35799 | 48.20% |
| 26.944 | 3.3064 | 2.50% |
| 27.56 | 3.23397 | 4.50% |
| 27.913 | 3.19379 | 3.20% |
| 28.666 | 3.11159 | 16.90% |
| 29.751 | 3.00056 | 6.70% |
| 30.444 | 2.93381 | 6.50% |
| 31.066 | 2.87647 | 4.10% |
| 31.706 | 2.81986 | 10.60% |
| 32.102 | 2.78599 | 0.70% |
| 33.171 | 2.69862 | 5.50% |
| 33.784 | 2.65098 | 2.60% |
| 34.586 | 2.59131 | 0.30% |
| 34.935 | 2.56625 | 0.80% |
| 35.963 | 2.49523 | 1.70% |
| 36.907 | 2.43353 | 1.30% |
| 37.415 | 2.40164 | 1.90% |
| 38.336 | 2.34605 | 0.50% |
| 38.773 | 2.32058 | 0.80% |
| 39.396 | 2.28533 | 1.30% |
| 39.654 | 2.27104 | 4.20% |

TABLE 5

Relative intenstities of diffracted radiation, measured angles, d-spacing obtained by XRPD for otho-topolin-mesylate

| Angle | d spacing | Rel. Intensity |
|---|---|---|
| 8.207 | 10.76503 | 1.5% |
| 8.365 | 10.56215 | 4.4% |
| 9.644 | 9.16369 | 7.4% |
| 9.822 | 8.99838 | 27.1% |
| 12.147 | 7.28043 | 81.2% |
| 14.156 | 6.25123 | 17.3% |
| 14.648 | 6.04243 | 14.3% |
| 15.391 | 5.75247 | 1.7% |
| 16.582 | 5.34174 | 8.1% |
| 16.629 | 5.32689 | 9.9% |
| 16.759 | 5.28574 | 22.8% |
| 16.961 | 5.22346 | 2.7% |
| 17.8 | 4.97896 | 20.7% |
| 17.834 | 4.96969 | 13.5% |
| 18.155 | 4.88242 | 16.1% |
| 18.287 | 4.84747 | 45.7% |
| 18.311 | 4.84129 | 44.5% |
| 18.566 | 4.77537 | 14.5% |
| 19.707 | 4.50128 | 13.2% |
| 20.296 | 4.37198 | 14.9% |
| 20.656 | 4.29662 | 26.5% |
| 20.797 | 4.26783 | 12.4% |
| 21.745 | 4.08382 | 18.2% |
| 22.724 | 3.90994 | 4.3% |

TABLE 5-continued

Relative intenstities of diffracted radiation, measured angles,
d-spacing obtained by XRPD for otho-topolin-mesylate

| Angle | d spacing | Rel. Intensity |
|---|---|---|
| 22.832 | 3.89183 | 5.9% |
| 23.271 | 3.81932 | 100.0% |
| 23.584 | 3.76928 | 1.9% |
| 24.136 | 3.68442 | 21.5% |
| 24.45 | 3.63775 | 14.9% |
| 24.497 | 3.63088 | 15.6% |
| 24.992 | 3.56012 | 11.8% |
| 25.149 | 3.53816 | 50.5% |
| 25.535 | 3.48558 | 3.8% |
| 25.897 | 3.43771 | 1.2% |
| 26.166 | 3.40301 | 2.7% |
| 26.793 | 3.32473 | 21.4% |
| 26.863 | 3.3162 | 12.6% |
| 27.16 | 3.28067 | 12.7% |
| 27.544 | 3.23576 | 12.2% |
| 28.019 | 3.18198 | 6.5% |
| 28.483 | 3.1312 | 6.2% |
| 28.558 | 3.12315 | 5.5% |
| 29.5 | 3.02553 | 18.3% |
| 29.98 | 2.97813 | 2.2% |
| 30.364 | 2.94131 | 8.5% |
| 30.451 | 2.9332 | 5.8% |
| 31.057 | 2.87724 | 1.9% |
| 31.189 | 2.86543 | 2.1% |
| 31.772 | 2.81412 | 4.8% |
| 31.852 | 2.80724 | 2.5% |
| 32.132 | 2.78343 | 1.6% |
| 32.714 | 2.73524 | 0.3% |
| 32.738 | 2.7333 | 0.6% |
| 33.533 | 2.67029 | 4.3% |
| 33.717 | 2.6561 | 3.6% |
| 33.921 | 2.64059 | 3.9% |
| 33.969 | 2.63703 | 3.7% |
| 34.322 | 2.61069 | 1.2% |
| 34.567 | 2.5927 | 2.8% |
| 34.616 | 2.58918 | 2.8% |
| 34.912 | 2.56788 | 3.4% |
| 34.884 | 2.56987 | 3.3% |
| 35.213 | 2.54666 | 1.0% |
| 35.852 | 2.50272 | 2.0% |
| 36.231 | 2.47738 | 2.3% |
| 36.614 | 2.45234 | 2.9% |
| 36.723 | 2.4453 | 2.6% |
| 37.02 | 2.42637 | 3.5% |
| 37.351 | 2.40559 | 1.3% |
| 38.549 | 2.33356 | 2.1% |
| 38.481 | 2.33752 | 5.0% |
| 38.532 | 2.33455 | 3.3% |
| 39.233 | 2.29444 | 4.1% |

TABLE 6

Relative intenstities of diffracted radiation, measured
angles, d-spacing obtained by XRPD for ortho-topolin

| Angle | d spacing | Rel. Intensity |
|---|---|---|
| 6.36 | 13.88626 | 100.0% |
| 12.609 | 7.01461 | 1.5% |
| 15.507 | 5.70981 | 12.2% |
| 15.559 | 5.6907 | 12.1% |
| 15.655 | 5.65596 | 13.9% |
| 16.71 | 5.30113 | 59.4% |
| 17.436 | 5.0821 | 45.2% |
| 18.947 | 4.6801 | 31.6% |
| 19.014 | 4.66371 | 35.6% |
| 19.1 | 4.643 | 43.8% |
| 19.97 | 4.44267 | 4.9% |
| 20.587 | 4.31072 | 11.0% |
| 23.786 | 3.73771 | 26.2% |

TABLE 6-continued

Relative intenstities of diffracted radiation, measured
angles, d-spacing obtained by XRPD for ortho-topolin

| Angle | d spacing | Rel. Intensity |
|---|---|---|
| 25.028 | 3.5551 | 18.8% |
| 25.225 | 3.52769 | 12.2% |
| 25.301 | 3.51731 | 12.8% |
| 25.889 | 3.4387 | 4.0% |
| 26.566 | 3.35267 | 37.7% |
| 27.318 | 3.26203 | 41.6% |
| 28.028 | 3.18093 | 1.2% |
| 28.188 | 3.16328 | 1.6% |
| 29.166 | 3.05934 | 14.9% |
| 29.491 | 3.02645 | 11.9% |
| 31.195 | 2.86489 | 3.4% |
| 31.596 | 2.82945 | 2.3% |
| 32.75 | 2.73234 | 6.4% |
| 32.792 | 2.72894 | 6.6% |
| 33.425 | 2.67866 | 3.1% |
| 33.651 | 2.66118 | 2.9% |
| 34.95 | 2.56521 | 4.4% |
| 35.816 | 2.50514 | 2.3% |

TABLE 7

Relative intenstities of diffracted radiation, measured
angles, d-spacing obtained by XRPD for kinetin mesylate

| Angle | d spacing | Rel. Intensity |
|---|---|---|
| 6.238 | 14.15724 | 100.0% |
| 6.971 | 12.67021 | 1.2% |
| 9.416 | 9.38466 | 1.1% |
| 10.148 | 8.70928 | 6.9% |
| 10.292 | 8.5877 | 3.5% |
| 10.603 | 8.33663 | 4.4% |
| 11.24 | 7.86575 | 2.1% |
| 11.475 | 7.70524 | 1.1% |
| 12.17 | 7.2667 | 2.5% |
| 12.377 | 7.14537 | 4.7% |
| 12.562 | 7.04094 | 4.6% |
| 13.128 | 6.73835 | 9.6% |
| 14.323 | 6.17907 | 3.1% |
| 15.051 | 5.88178 | 4.5% |
| 15.176 | 5.83327 | 1.1% |
| 15.799 | 5.60469 | 3.3% |
| 16.203 | 5.46585 | 6.8% |
| 17.095 | 5.18275 | 2.1% |
| 17.327 | 5.11395 | 2.2% |
| 17.515 | 5.05948 | 2.0% |
| 18.665 | 4.75008 | 14.0% |
| 18.882 | 4.69604 | 38.7% |
| 19.835 | 4.47249 | 26.0% |
| 20.119 | 4.4101 | 23.2% |
| 20.389 | 4.35212 | 46.9% |
| 20.668 | 4.29413 | 10.2% |
| 20.839 | 4.25928 | 14.0% |
| 21.397 | 4.14938 | 6.6% |
| 21.976 | 4.04131 | 3.3% |
| 22.634 | 3.92529 | 27.4% |
| 22.76 | 3.90391 | 17.3% |
| 22.981 | 3.86685 | 22.7% |
| 23.923 | 3.71668 | 33.8% |
| 24.132 | 3.68494 | 13.2% |
| 24.844 | 3.58099 | 3.8% |
| 24.978 | 3.5621 | 5.8% |
| 25.218 | 3.52875 | 3.4% |
| 26.172 | 3.40223 | 1.5% |
| 26.445 | 3.36765 | 4.7% |
| 26.65 | 3.34226 | 9.3% |
| 26.861 | 3.31649 | 4.6% |
| 27.417 | 3.25044 | 1.9% |
| 27.672 | 3.22113 | 39.9% |
| 27.755 | 3.21163 | 72.5% |

TABLE 7-continued

Relative intensities of diffracted radiation, measured angles, d-spacing obtained by XRPD for kinetin mesylate

| Angle | d spacing | Rel. Intensity |
|---|---|---|
| 28.062 | 3.17716 | 9.0% |
| 28.536 | 3.12548 | 2.0% |
| 29.344 | 3.04125 | 0.5% |
| 30.394 | 2.93849 | 1.1% |
| 31.452 | 2.84201 | 0.9% |
| 32.349 | 2.76522 | 3.0% |
| 32.49 | 2.75361 | 4.5% |
| 32.868 | 2.72281 | 4.2% |
| 34.527 | 2.59567 | 0.8% |
| 34.779 | 2.5774 | 1.4% |
| 35.09 | 2.55526 | 1.4% |
| 35.526 | 2.5249 | 0.7% |
| 36.152 | 2.48262 | 0.7% |
| 37.197 | 2.41524 | 0.9% |
| 37.472 | 2.39811 | 1.2% |
| 37.808 | 2.37761 | 1.7% |
| 38.303 | 2.34798 | 0.9% |
| 39.807 | 2.26269 | 0.5% |

TABLE 8

Relative intenstities of diffracted radiation, measured angles, d-spacing obtained by XRPD for kinetin

| Angle | d spacing | Rel. Intensity |
|---|---|---|
| 6.418 | 13.76056 | 0.2% |
| 7.098 | 12.44319 | 100.0% |
| 11.394 | 7.75957 | 0.5% |
| 12.7 | 6.96462 | 0.3% |
| 14.157 | 6.25098 | 0.4% |
| 15.491 | 5.71548 | 0.0% |
| 17.176 | 5.15854 | 10.2% |
| 19.236 | 4.61044 | 5.7% |
| 19.726 | 4.49692 | 0.3% |
| 20.872 | 4.25261 | 3.6% |
| 21.345 | 4.15939 | 0.6% |
| 23.024 | 3.85973 | 4.4% |
| 23.553 | 3.77427 | 3.1% |
| 24.12 | 3.68676 | 1.6% |
| 24.812 | 3.58546 | 1.2% |
| 25.478 | 3.49323 | 1.5% |
| 26.028 | 3.42071 | 0.7% |
| 26.976 | 3.30263 | 6.8% |
| 27.391 | 3.2535 | 0.4% |
| 28.441 | 3.13568 | 7.8% |
| 28.699 | 3.10812 | 1.3% |
| 29.636 | 3.01194 | 0.7% |
| 30.132 | 2.96351 | 0.1% |
| 31.561 | 2.83251 | 0.4% |
| 32.169 | 2.7803 | 0.1% |
| 33.332 | 2.6859 | 0.2% |
| 34.734 | 2.58068 | 0.7% |
| 35.37 | 2.53568 | 0.2% |
| 36.032 | 2.49063 | 0.3% |
| 36.686 | 2.44772 | 0.1% |
| 38.07 | 2.3618 | 0.1% |
| 38.712 | 2.32411 | 0.3% |

Example 10: Characterization of Crystalline Cytokinin Mesylate Salts By $^1$H Nuclear Magnetic Resonance (NMR)

$^1$H Nuclear Magnetic Resonance (NMR): $^1$H NMR was performed on a JEOL 500 SS operating at the temperature of 300 K and a frequency of 500.13 MHz. The samples were prepared by dissolving the compounds in DMSO-d6. Tetramethylsilane (TMS) was used as an internal standard. Calibration of chemical shift related to shift of residual solvent peak in $^1$H DMSO-$d_6$, 2.50 ppm. Each sample was prepared in ca. 5 mg concentration. Chemical shifts identified in the spectra of selected cytokininmesylate crystalline salt respond to described chemical compound and are as follows:

meta-topolin mesylate (6-(3-hydroxybenzylamino)purine mesylate): $^1$H NMR (500 MHz, DMSO-$D_6$) δ 9.55 (s, 1H), 8.64 (s, 1H), 8.53 (s, 1H), 7.28 (t, J=7.9 Hz, 1H), 7.00-6.94 (m, 2H), 6.87 (d, J=8.2 Hz, 1H), 4.81 (s, 2H), 2.35 (s, 3H).

BAP mesylate: $^1$H NMR (500 MHz, DMSO-D6) δ 9.66 (s, 1H), 8.64 (s, 1H), 8.54 (s, 1H), 7.40-7.29 (m, 5H), 7.26 (t, J=7.1 Hz, 1H), 4.80 (d, J=5.9 Hz, 2H), 2.35 (s, 3H).

kinetin mesylát: $^1$H NMR (500 MHz, DMSO-$D_6$) δ 9.53 (s, 1H), 8.69 (s, 1H), 8.56 (s, 1H), 7.65 (s, 1H), 6.45 (s, 2H), 4.85 (s, 2H), 2.40-2.34 (m, 3H).

ortho-topolin mesylate: $^1$H NMR (500 MHz, DMSO-$D_6$) δ 9.27 (s, 1H), 8.60 (s, 1H), 8.46 (s, 1H), 7.18 (d, J=7.2 Hz, 1H), 7.14-7.07 (m, 1H), 6.83 (d, J=7.9 Hz, 1H), 6.74 (t, J=7.3 Hz, 1H), 4.69 (d, J=5.6 Hz, 2H), 2.29 (s, 3H).

(Z)-zeatin (cis-zeatin) mesylate: $^1$H NMR (DMSO-d6): δ 1.67 (s, 3H); 3.81 (d, 2H, J=5.2); 4.15 (m, 2H); 4.72 (t, 1H, J=5.55); 5.55 (t, 1H, J=6.8); 7.67 (bs, 1H); 8.07 (s, 1H); 8.19 (s, 1H)

(E)-zeatin (trans-zeatin) mesylate: $^1$H NMR (DMSO-d6): 1.69 (s, 3H); 3.80 (d, 2H, J=7.0); 4.15 (bs, 2H); 4.75 (t, 1H); 5.53 (t, 1H, J=7.0); 8.09 (s, 1H); 8.19 (s, 1H)

Dihydrozeatin (racemic) mesylate: $^1$H NMR (DMSO-d6): 1.00 (d, 3H, J=6.8); 1.51 (m, 1H); 1.75 (m, 1H); 1.85 (m, 1H); 3.44 (dd, 1H, J=11.0, J=6.0); 3.48 (dd, 1H, J=11.0); 3.66 (m, 2H); 8.06 (s, 1H), 8.22 (s, 1H)

Isopentenyladenin mesylate: $^1$H NMR (DMSO-d6): 1.67 (s, 3H), 1.70 (s, 3H), 4.08 (br s, 1H), 5.31 (s, 1H), 7.55 (bs, 1H), 8.04 (s,1H), 8.16 (s.1H)

When compared to chemical shifts of their respective bases (BAP, meta-topolin, ortho-topolin, kinetin, Z-zeatin, E-zeatin, dihydrozeatin, isopentenyladenine) that are known, described compounds, significant differences are apparent, especially of those chemical shifts that are in the vicinity of protonated hydrogens.

Example 11: Single Crystal X-Ray Diffraction of Crystalline Meta-Topolin Mesylate Salt and Description of Molecular Structure Single Crystal Preparation: Crystals were grown from solutions of crystalline meta-topolin mesylate salt (ca. 100 mg) dissolved in metanol (40 $cm^3$). The solution was then allowed to slowly evaporate through pierced parafilm. Translucent crystals were visible after ca. 14 days of evaporation.

Single Crystal X-Ray Diffraction: Suitable crystal of the sample was selected for data collection. Diffraction data were collected using four/circle diffractometer Supernova with mirror-collimated Cu/Kα radioation from a micro-focus sealed X-ray tube, equipped with the CCD areal detector Atlas S2 operation at 94.94 (13) K.

On indexing the data set, the crystal structure was determined to be a centrosymmetric dimer linked by below discussed hydrogen bonding. Crystal system was identified as monoclinic with Pna21 space group and with the following cell dimensions: a=14.9313 (1), b=7.8302 (3), c=25.1594 (1) Å, α=90°, β=90°, γ=90° and cell volume V=2941.51 Å$^3$. Data collection, reduction and absorption corrections for all compounds were carried out using CrysAlisPro software (Rigaku Oxford Diffraction, 2018) CrysAlis version 1.171.40.53). The asymmetric unit of the title compound is formed by a 6-(3-hydroxybenzylamino) purinium cation and a mesylate anion. Hydrogen atoms attached to carbon were placed in calculated positions. Some hydrogen atoms attached to oxygen could be located in difference map, Intermolecular hydrogen bonds between N—H atom of purine and oxygen atom of mesylate anion connect two molecules as centrosymmetric dimers. These hydrogen bonds stabilize the system and connect N6a . . . H6b of purine structure with Ola of mesylate anion, N7a . . . H7a of purine structure with O5b of mesylate anion, O4b . . . H4b of hydroxyl attached to benzyl ring of meta-topolin with O5b of mesylate anion and also 04a . . . H4a of meta/topolin with O1b of mesylate (FIG. 4).

The final 'conventional' R-factor [based on F and 5945 reflections with [$F^2$>2σ($F^2$)] was 0.0257. The single crystal structure of crystalline meta-topolin mesylate crystalline salt shows that the compound has general formula of $C_{13}H_{15}N_5O_4S$ based on 6-(3-hydroxybenzylamino) purinium cation and mesylate anion. Centrosymmetric dimers are bond together by a number of above listed intermolecular hydrogen bonds that are mainly realized between protonized cation and mesylate anion that contributes to excellent solubility of the compound in water. Important torsion angles, that also have impact on physical properties and solubility of the compounds, are strongly influenced by the formation of such thick network of intermolecular hydrogen bonding.

Example 12: Single Crystal X-Ray Diffraction and Structural Analysis of Ortho-Topolin Mesylate Crystalline Salt Single Crystal Preparation: Crystals were grown from solutions of crystalline ortho-topolin mesylate salt (ca. 100 mg) dissolved in metanol (30 $cm^3$). The solution was then allowed to slowly evaporate through pierced parafilm. Translucent crystals were visible after ca. 7 days of evaporation.

Single Crystal X-Ray Diffraction: Suitable crystals of the sample were selected for data collection. Diffraction data were collected using four/circle diffractometer Xcalibur Gemini ultra with Cu/Kα radiation (λ=1.54184 Å) with graphite monochromator equipped with the CCD area detector Atlas S2 operation at 120.01 (10) K.

Figure 5:
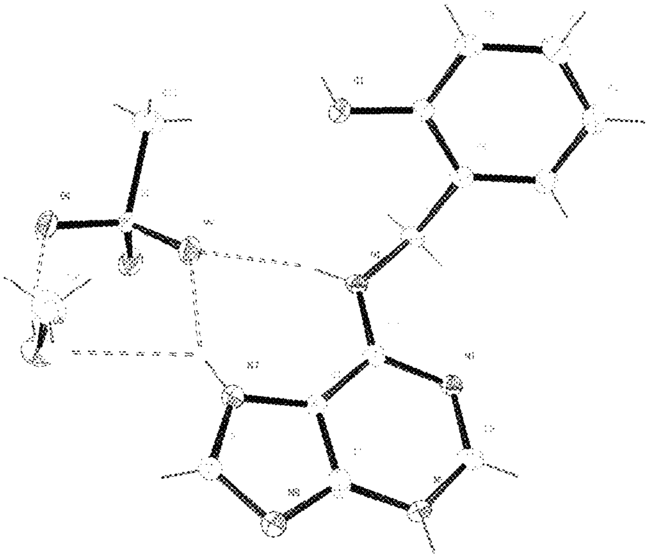
FIG. 5 shows molecular structure of ortho-topolin mesylate crystalline salt including intermolecular hydrogen bond network obtained by single crystal X-ray diffraction.

Crystal system was identified as monoclinic with $P2_1/c$ space group and with the following cell dimensions: a=10.3822 (4), b=21.0265 (5), c=8.1025 (2) Å, α=90°, β=107.466°, γ=90° and cell volume V=1688.21 (9) $Å^3$. The structure model was found using Superflip or SHELXT and refined by full-matrix least-squares by JANA2006 software. Data collection, reduction and absorption corrections for all compounds were carried out using CrysAlisPro Software (Rigaku, Oxford Diffraction, 2018, CrysAlis version 1.171.40.35a). The asymmetric unit of the title compound is formed by 6-(2-hydroxybenzylamino)purinium cation and mesylate anion and one molecule of methanol solvent. Hydrogen atoms attached to carbon were placed in calculated positions. Some hydrogen atoms attached to oxygen could be located in difference maps. Intermolecular hydrogen bonds between N—H atom of purine and oxygen atom of mesylate anion connectmesylate anions with 6-(2-hydroxybenzylamino)purinium cations and the cation is also connected via hydrogen bonding with methanol solvent. Hydrogen bonds network stabilizes the system and connect mainly N6 . . . H6 atom of purine structure with O2 of mesylate anion and also N7 . . . H7 of purine structure with O2 of mesylate anion. Further, there are linked O5 . . . H5 of methanol to O2 of mesylate anion and concurrently to N7 . . . H7 of purine moiety as shown at FIG. 5. O1 . . . H1 of hydroxyl attached to benzene ring is linked with O3b . . . H3b atom of the mesylate anion that compensates the next 6-(2-hydroxybenzylamino)purinium cation (FIG. 5). The final 'conventional' R-factor [based on F and 3024 reflections with [$F^2$>2σ($F^2$)] was 0.0324. The single crystal structure of crystalline ortho-topolin mesylate crystalline salt shows that the compound has general formula of $C_{14}H_{19}N_5O_5S$, 2-hydroxybenzylaminopurinium cation and mesylate anion, accompanied with a molecule of methanol solvent. Centrosymmetric dimers of asymmetric unit are bonded together by a network of the above listed intermolecular hydrogen bonds that are mainly realized between protonized cation and mesylate anion and also include methanol solvent and that contribute to good solubility of the compound in water. Hydrogen atom placement inferred from X-ray data is usually regarded as tentative, but the position of particular molecules within the frame of the structure is persuasive. Besides, important torsion angles, that also have impact on physical properties and solubility of the compounds, are stongly influenced by the formation of such thick network of intermolecular hydrogen bonding.

Example 13: Aqueous Solubility of Meta-Topolin Mesylate Salt

Aqueous solubility was measured using the following protocol. Supersaturated solution of meta-topolin mesylate salt was prepared. The solutions were filtered off from visible undissolved particles of the salt to obtain homogenic saturated solution. Saturated solution was diluted 1:10 000 and measured using HPLC Alliance Waters 2690 with C18 Symmetry column with the diameter 2.1 mm and 150 mm length with a porosity of 5 μm. The sample was dissolved in the mobile phase (MeOH: $HCOONH_4$-1:9). The sample was washed with a methanol gradient (10-90%, 35 min) at pH 4 and a flow rate of 0.3 ml/min. The absorbances of the components were detected in the UV region at 210-400 nm. The peak area of meta-topolin mesylate salt was 595 027. The standard was measured as shown in the Table 9 below, Obtained peak area was compared to area peaks measured at certain concentration and the final concentration of saturated solution was determined

TABLE 9

Peak areas for certain concentrations of meta-topolin salts in water.

| c (μM) | Peak area of meta-topolin mesylate |
|---|---|
| 10 | 261426 |
| 25 | 637311 |
| 50 | 1253289 |

It means that the concentration of meta-topolin mesylate crystalline salt is approximately 24010,81 μM, it means 24,011 mM (8 mg/ml), which is one order of magnitude better than solubility defined for meta-topolin base. Meta-topolin is reported to exhibit an aqueous solubility of <0.25 mg/ml, we determined the concentration of saturated solution of meta-topolin to be only 0.06 mg/ml. Solubility of other cytokinin (CK) mesylates was also determined by this method and the concentrations of saturated solutions are given below in Table 10:

TABLE 10

| Free CK base | c of free CK base [mM] | CK mesylate | c of CK mesylate [mM] |
|---|---|---|---|
| 6-(2-hydroxybenzylamino)purine (o-topolin) | 0.03 | 6-(2-hydroxybenzylamino)purine mesylát | 82.3 |
| 6-(3-hydroxybenzylamino)purine (m-topolin) | 0.06 | 6-(3-hydroxybenzylamino)purine mesylate | 24.011 |
| 6-(benzylamino)purine (BAP) | 0.37 | 6-(benzylamino)purine mesylate | 354.13 |
| 6-(3-methoxybenzylamino)purine | 0.21 | 6-(3-methoxybenzylamino)purine mesylate | 47.54 |
| kinetin | 0.14 | kinetin mesylate | 92.56 |

Example 14: Solubility of Meta-Topolin Mesylate Compared to Meta-Topolin in Organic Solvents Solubility in organic solvents was measured using the following protocol. Approximately 25 mg portions of meta-topolin and crystalline meta-topolin mesylate salt were placed in 48 different vials, separately. 5 volume aliquots of each solvent were added progressively (repeatedly) to the vials. After each addition, the mixture was checked for dissolution and if no dissolution was visible, the procedure was continued until dissolution was observed, or until 50 volumes have been added. The results are shown in Table 11. While the solubility in polar solvents such as water or alcohols differ significantly, almost no changes are observed in other organic solvents.

TABLE 11

Solubility of meta-topolin mesylate and comparison with meta-topolin in various organic solvents

| Solvent | Meta-topolin mesylate | Meta-topolin |
|---|---|---|
| methanol | 0.7 mg/ml | 5 mg/ml |
| ethanol | 0.4 mg/ml | 5 mg/ml |
| DMF | 6 mg/ml | 6 mg/ml |
| DMSO | 22 mg/ml | 24 mg/ml |
| aceton | 0.4 mg/ml | 0.4 mg/ml |
| heptane | <0.1 mg/ml | <0.1 mg/ml |
| acetonitrile | <0.25 mg/ml | <0.25 mg/ml |

Figure 6:
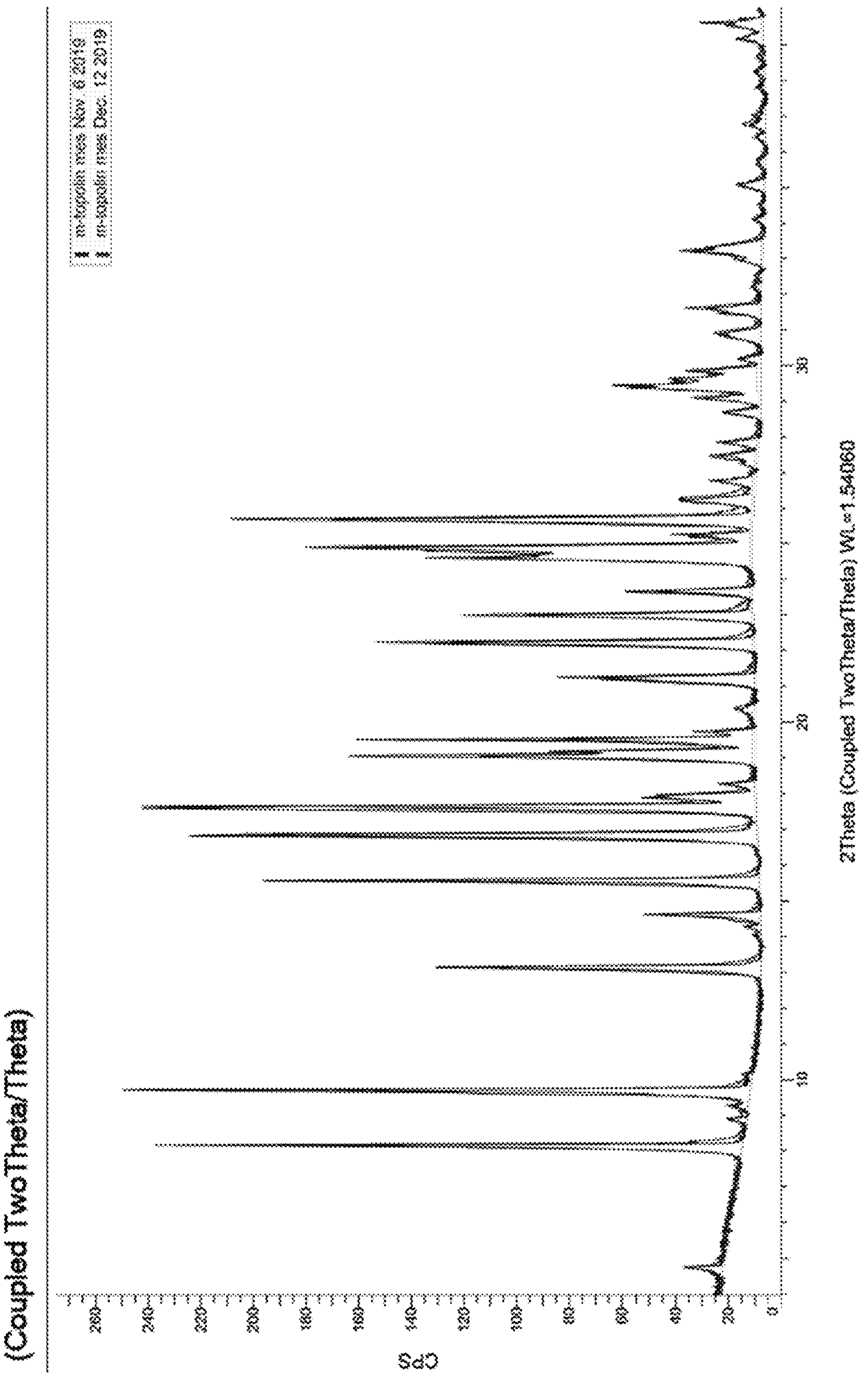
FIG. 6: shows XRPD pattern of meta-topolin mesylate crystalline salt one month after storage in solid form.

Example 15: Storage Stability Study of Meta-Topolin Mesylate Crystalline Salt 50 mg sample of crystalline meta-topolin mesylate crystalline salt was placed in an eppendorf tube and sealed. The sample was kept at 25° C. for 60 days. No color change was noted during the storage period. XRPD of samples were taken after 60 days to investigate any solid form change. FIG. 6 shows the XRPD patterns of the initial sample and samples of crystalline meta-topolin mesylate crystalline salt after 60 days. The test did not reveal any changes in XRPD spektra, or change in color after 60 days of the compound storage period in solid form.

Example 16: Disproportionation Stability Study of Meta-Topolin Mesylate Crystalline Salt A 50 mg sample of crystalline meta-topolin mesylate crystalline salt was slurried in 250 µL distilled water for ca. 48 hours and then checked by XRPD for disproportionation. No signs of disproportionation were observed.

Example 17: In Vitro Cytotoxic Activity of Crystalline Cytokinin Mesylate Salts (Metabolisation of Calcein)

Because toxic compounds adversely affect cell metabolic processes, many standard cytotoxicity assays are based on measuring the rate of metabolism of various artificial substrates. The resulting product is then quantified, for example, by spectrometry. Assays can be easily modified for use in 96-well plates, A microtiter assay based on the quantification of Calcein AM metabolism was used to evaluate the cytotoxicity of cytokinins, for example meta-topolin, ortho-topolin, kinetin, BAP or its mesylate salts, but also a number of other cytokinin mesylate derivatives according to the invention. The test is widely used in drug screening programs and in chemosensitivity testing. In living cells, Calcein AM is enzymatically hydrolyzed and the accumulation of the resulting calcein is manifested by green fluorescence. The following cell lines—RPMI 8226 (multiple myeloma), CEM (T-lymphoblastic leukemia), K562 (chronic myeloid leukemia), HL-60 (promyelocytic, leukemia), MCF-7 (breast adenocarcinoma), HeLa (cervical cancer), G361 (malignant melanoma), HOS (human osteosarcoma) and BJ (human foreskin fibroblasts)—were obtained from the American Type Culture Collection (Manassas, VA, USA). These cells were maintained in standard DMEM or RPMI medium (Sigma, MO, USA) supplemented with heat-inactivated fetal bovine serum (10%) with 2 mM L-glutamine and penicillin-streptomycin (1%) under standard cell culture conditions (37° C., 5% $CO_2$ in a humid environment) and subcultured two or three times a week using a standard trypsinization procedure. Approximately 10,000 cells in 80 µl of medium were seeded in a 96-well microtiter plate. After 12 hours of incubation, the compounds to be tested were added in 20 µl aliquots. Control cultures were treated with DMSO alone. The final concentration of DMSO in the medium did not exceed 0.5%. Serial, 3-fold dilutions (six in total, peak concentrations in 166 µM incubations) of each compound were tested. After 72 hours of incubation, Calcein AM solution (Molecular Probes) was added to a final concentration of 1 µg/ml and the cells were incubated for another hour. Free calcein fluorescence was then quantified using a Fluoroscan Ascent fluorometer (Microsystems), and the percentage of surviving cells in each well was calculated by dividing the OD obtained from each cell by the exposed cells by the mean OD obtained from control wells×100%, Finally, $IC_{50}$ values (concentration causing a 50% decrease in cellular esterase activity) were calculated for each compound generated from dose-response curves (Kryštof et al., 2005, Bioorg. Med. Chem. Lett. 12, 3283-3286). The $IC_{50}$ values reported here are averages obtained from at least three independent experiments, where the individual replication values fell within 20% of the average. Growth inhibition was calculated using the following equation: $IC_{50}$=(mean $FD_{well\ exposed\ to\ drug}$−mean $FD_{blank}$)/(mean $FD_{control\ well}$−mean $FD_{blank}$)×100%.

Cytoxicity of compounds was tested on panel of cell lines of different histogenetic and species origin. As shown in Table 12. $IC_{50}$ of cytokinin derivatives exceeded maximal concentration tested which shows that the compounds can be applied at concentrations causing desired effect without negative side effects. For comparison, mesylate salts exhibited similar or even lower cytotoxicity than free bases.

TABLE 12

Cytotoxic activity of cytokinin bases and their mesylate salts expressed as $IC_{50}$ values in a 3-day Calcein-AM assay. Presented values are averages of at least 3 independent experiments, where individual replicates fall into 20% interval around the average.

| | Cell line tested/$IC_{50}$ (μmol/L) | | | | | | |
|---|---|---|---|---|---|---|---|
| Compound | HOS | K-562 | MCF7 | NIH-3T3 | G-361 | CEM | HL60 |
| Kinetin | >166.7 | >166.7 | >166.7 | | | 155.1 | |
| Kinetin mesylate | | >166.7 | >166.7 | | | >166.7 | |
| iP | >166.7 | 146.9 | >166.7 | | | 92.2 | >166.7 |
| iP mesylate | | 162.2 | >166.7 | | | 127.9 | |
| BAP | >166.7 | 138.9 | 166.1 | | | >166.7 | >166.7 |
| BAP mesylate | | >166.7 | >166.7 | >166.7 | | >166.7 | |
| Cis-zeatin (cZ) | >166.7 | >166.7 | >166.7 | | | >166.7 | >166.7 |
| cZ mesylate | | >166.7 | >166.7 | | | >166.7 | |
| Dihydrozeatin (DHZ) | >166.7 | >166.7 | >166.7 | | | >166.7 | >166.7 |
| DHZ mesylate | | >166.7 | >166.7 | | | >166.7 | |
| meta-topolin (mT) | >166.7 | 128.4 | >166.7 | | >166.7 | 90.1 | 79.2 |
| mT mesylate | | 141.7 | >166.7 | | | >166.7 | |
| ortho-topolin (oT) | >166.7 | >166.7 | >166.7 | | 103.4 | 69.2 | 78.0 |
| oT mesylate | | >166.7 | >166.7 | | | 89.4 | |
| 2FBAP | >166.7 | 136.1 | >166.7 | | 106.4 | 98 | |
| 2FBAP mesylate | >166.7 | 70.7 | >166.7 | | | 99.5 | 126.5 |
| 2ClBAP | 84.9 | 101.0 | 164.1 | >166.7 | 56.6 | 58.4 | 109.6 |
| 2ClBAP mesylate | 100.4 | 90.4 | 128.4 | | | 112.5 | |
| 3ClBAP | >166.7 | >166.7 | >166.7 | | 148.6 | >166.7 | >166.7 |
| 3ClBAP mesylate | | >166.7 | | | | >166.7 | |
| 3FBAP | >166.7 | 105.2 | 163.2 | | >166.7 | >166.7 | >166.7 |
| 3FBAP mesylate | | 135.7 | >166.7 | | | >166.7 | |
| 4FBAP | >166.7 | >166.7 | >166.7 | | >166.7 | 66.4 | 59.2 |
| 4FBAP mesylate | | >166.7 | >166.7 | | | | |
| 3MeOBAP | >166.7 | >166.7 | >166.7 | >166.7 | 124.7 | >166.7 | >166.7 |
| 3MeOBAP mesylate | | >166.7 | >166.7 | | | >166.7 | |
| 4MeOBAP | >166.7 | >166.7 | >166.7 | >166.7 | 166.7 | >166.7 | >166.7 |
| 4MeOBAP mesylate | >166.7 | 118.0 | >166.7 | | | >166.7 | |
| 2MBAP | >166.7 | 156.6 | >166.7 | | >166.7 | >166.7 | >166.7 |
| 2MBAP mesylate | | >166.7 | >166.7 | | | >166.7 | |
| 4ClBAP | >166.7 | >166.7 | >166.7 | | | >166.7 | >166.7 |
| 4ClBAP mesylate | | >166.7 | >166.7 | | | >166.7 | |
| 2MeOBAP | >166.7 | 115.8 | 153.0 | | | 63.4 | >166.7 |
| 2MeOBAP mesylate | | 116.7 | >166.7 | | | 98.2 | |
| 2OH3MeOBAP | | >166.7 | 26.6 | | | 41.6 | 64.3 |
| 2OH3MeOBAP mesylate | | >166.7 | 32.1 | | | 51.0 | 67.8 |
| trans-zeatin (tZ) | | >166.7 | >166.7 | | | >166.7 | >166.7 |
| tZ mesylate | | >166.7 | >166.7 | | | >166.7 | >166.7 |

Example 18: In Vitro Cytotoxicity of Novel Derivatives for Non-Cancer Cells, Skin Fibroblasts (BJ) and Keratinocytes (HaCaT, ARPE-19), Evaluated Using Resazurine Reduction Assay Resazurin (7-Hydroxy-3H-phenoxazin-3-one 10-oxide) is a blue weakly fluorescent compound that is irreversibly reduced into red highly fluorescent resofurin by mitochondria. It is used for viability testing of both bacterial and eukaryotic cells. The effect of the novel compounds in several concentrations (maximum concentraton of 100 microM and 5 1.5-fold dilutions) on viability of skin fibroblasts BJ, keratinocytes HaCaT and retinal epitelium cells ARPE-19 was evaluated after 72 hour treatment and results are given in Table 13. The cells were maintained in standard cultivation conditions (5.5% CO2, 37° C., 100% humidity). Cultivation medium was DMEM with 10% FBS. Before the experiment, the cells were subcultured for 2 weeks. For the cytotoxicity evaluation, the cells were trypsinized and pipetted into 96 well plates (5000 cells per well in 80 microliters). After 24 hours, 5× concentrated solutions of the tested compounds in the medium were added. After 72 hours, 10× concentrated solution of resazurin in the medium (prepared from 1000× concentrated DMSO solution) was added to the cells into the final concentration of 0.0125 mg/ml. Fluorescence (ex=570 nm, em=610 nm) was measured after 1 hour (ARPE-19) or 3 hours (HaCaT and BJ) of incubation and the results are shown in Table 13. $IC_{50}$ values were calculated from dose response curves using drc library for R programming environment.

TABLE 13

| Cytotoxicity for Fibroblasts ($GI_{20}$, μM) | | | |
|---|---|---|---|
| Compound | BJ | HaCaT | ARPE-19 |
| Kinetin | >100 | >100 | >100 |
| Kinetin mesylate | >100 | >100 | >100 |
| iP | 100 | >100 | >100 |
| iP mesylate | 149.3 | >100 | >100 |

TABLE 13-continued

| Cytotoxicity for Fibroblasts ($GI_{20}$, μM) | | | |
|---|---|---|---|
| Compound | BJ | HaCaT | ARPE-19 |
| BAP | 137.5 | >100 | >100 |
| BAP mesylate | >100 | >100 | >100 |
| meta-topolin (mT) | >100 | >100 | >100 |
| mT mesylate | >100 | >100 | >100 |
| ortho-topolin (oT) | 98.7 | >100 | >100 |
| oT mesylate | >100 | >100 | >100 |
| trans-zeatin (tZ) | >100 | >100 | >100 |
| tZ mesylate | >100 | >100 | >100 |

Example 19: Inhibition of Senescence by Cytokinin Mesylate Salts Tested on Winter Wheat Leaf Segments Seeds of winter wheat, *Triticum aestivum* cv. Hereward, were washed under running water for 24 hours and then sown on vermiculite soaked with Knop's solution. They were placed in a growth chamber at 25° C. with a 16/8 h light/dark period at 50 $\mu mol{\cdot}m^{-2}{\cdot}s^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 μl of each tested compound solution. The entire plate was inserted into a plastic box lined with paper tissues soaked in distilled water to prevent leaf sections from drying out. After 96 h incubation in the dark at 25° C., the leaves were removed and chlorophyll extracted by heating at 80° C. for 10 min in 5 ml of 80% ethanol (v/v). The sample volume was then restored to 5 ml by the addition of 80% ethanol (v/v). The absorbance of the extract was recorded at 665 nm. In addition, chlorophyll extracts from fresh leaves and leaf tips incubated in deionised water were measured. From the obtained data, the concentration with highest activity was selected for each tested compound. Relative activity of the compound at this concentration was calculated (Tab. 3). The activity obtained for $10^{-4}$ M 6-benzylaminopurine (BAP) was postulated as 100%. The values shown are means of five replicates and the whole experiment was repeated twice. The tested cytokinin bases were dissolved in dimethylsulfoxide (DMSO) and the solution brought up to $10^{-3}$ M with distilled water. Cytokinin mesylate salts which are more water-soluble (BAP mesylate, meta-topolin mesylate and kinetin mesylate) could be directly dissolved to form a $10^{-3}$ M solution in distilled water. This stock was further diluted in distilled water to concentrations ranging from $10^{--8}$ M to $10^{--4}$ M. The final concentration of DMSO if used did not exceed 0.2% and therefore did not affect biological activity in the assay system used. The results in Table 14 show that the new cytokinin mesylate salts led to an increase of the cytokinin activity in the senescence bioassay in comparison to the classical cytokinin free bases.

TABLE 14

Effect of new cytokinin mesylates on retention of chlorophyll in excised wheat leaf tips. Standard deviations are of the mean for 10 replicate determination.

| Tested compound | concentration with highest activity ($mol \cdot l^{-1}$) | activity (%) [$10^{-4}$ $mol \cdot l^{-1}$ BAP = 100%] |
|---|---|---|
| 6-benzylaminopurine (BAP) | $10^{-4}$ | 100 (±9.5) |
| BAP mesylate | $10^{-4}$ | 108 (±10.7) |
| 6-(2-hydroxybenzylamino)purine - ortho-topolin (oT) | $10^{-4}$ | 67 (±6.7) |
| oT mesylate | $10^{-4}$ | 69 (±9.1) |
| 6-(3-hydroxybenzylamino)purine - meta-topolin (oT) | $10^{-4}$ | 117 (±11.4) |
| 3-MeOBAP | $10^{-4}$ | 101 (±9) |
| 3-MeoBAP mesylate | $10^{-4}$ | 125 (±8) |
| mT mesylate | $10^{-4}$ | 109 (±13) |
| Kinetin | $10^{-4}$ | 103 (±12) |
| Kinetin mesylate | $10^{-4}$ | 110.9 (±11) |
| isopentenyladenine (iP) | $10^{-4}$ | 93 (±10.8) |
| iP mesylate | $10^{-4}$ | 95 (±12.6) |
| Dihydrozeatin (DHZ) | $10^{-4}$ | 81 (±9.2) |
| DHZ mesylate | $10^{-4}$ | 82 (±9.7) |
| trans-zeatin (tZ) | $10^{-4}$ | 110 (±13.2) |
| tZ mesylate | $10^{-4}$ | 114 (±12.8) |
| 2FBAP | $10^{-4}$ | 169 (±20) |
| 2FBAP mesylate | $10^{-4}$ | 175 (±18) |
| 3FBAP | $10^{-4}$ | 200 (±25) |
| 3FBAP mesylate | $10^{-4}$ | 210 (±23) |
| 4FBAP | $10^{-4}$ | 95.5 (±3.5) |
| 4FBAP mesylate | $10^{-4}$ | 98 (±12) |
| 2ClBAP | $10^{-4}$ | 116.5 (±6.5) |
| 2ClBAP mesylate | $10^{-4}$ | 122 (±13) |
| 3ClBAP | $10^{-4}$ | 82 (±2) |
| 3ClBAP mesylate | $10^{-4}$ | 82 (±7) |
| 2MeOBAP | $10^{-4}$ | 269 (±12) |
| 2MeOBAP mesylate | $10^{-4}$ | 271 (±18) |
| 3MeOBAP | $10^{-4}$ | 178 (±16) |
| 3MeOBAP mesylate | $10^{-4}$ | 184 (±21) |

TABLE 14-continued

Effect of new cytokinin mesylates on retention of chlorophyll in excised wheat leaf tips. Standard deviations are of the mean for 10 replicate determination.

| Tested compound | concentration with highest activity (mol · $l^{-1}$) | activity (%) [$10^{-4}$ mol · $l^{-1}$ BAP = 100%] |
|---|---|---|
| 2MBAP | $10^{-4}$ | 158 (±29) |
| 2MBAP mesylate | $10^{-4}$ | 157 (±14) |
| 6-(2.4-difluorobenzylamino)purine (2.4diFBAP) | $10^{-5}$ | 139 (±2) |
| 2.4diFBAP mesylate | $10^{-5}$ | 141 (±13) |
| 6-(3.5-difluorobenzylamino)purine (3.5diFBAP) | $10^{-5}$ | 156 (±4) |
| 3.5diFBAP mesylate | $10^{-5}$ | 168 (±9) |

Example 20: Stimulation Effect of the New Cytokinin Mesylates on Plant Cell Division Stimulation effect of the cytokinin mesylates was tested in tobacco callus biotest using cytokinin dependent tobacco callus. Cytokinin-dependent tobacco callus *Nicotiana tabacum* L. cv. Wisconsin 38 was maintained at 25° C. in darkness on modified MS medium, containing per 1 liter: 4 μmol nicotinic acid, 2.4 μmol pyridoxine hydrochloride, 1.2 μmol thiamine, 26.6 μmol glycine, 1.37 μmol glutamine, 1.8 μmol myo-inositol, 30 g of sucrose, 8 g of agar, 5.37 μmol NAA and 0.5 μmol BAP. Subcultivation was carried out every three weeks. Fourteen days before the bioassay, the callus tissue was transferred to the media without BAP. Biological activity was determined from the increase in fresh callus weight after four weeks of cultivation. Five replicates were prepared for each cytokinin concentration and the entire test was repeated twice. From the obtained data, the concentration with highest activity was selected for each compound tested. Relative activity of the compound at this concentration was calculated (Tab. 15). The activity obtained for $10^{-5}$ M 6-benzylaminopurine (BAP) was postulated as 100%. The cytokinin bases to be tested were dissolved in dimethylsulfoxide (DMSO) and the solution brought up to $10^{-3}$ M with distilled water. The mesylate salts were dissolved directly in distilled water. This stock was further diluted in the respective media used for the biotest to concentrations ranging from $10^{-8}$ M to $10^{-4}$ M. The final concentration of DMSO did not exceed 0.2% and therefore did not affect biological activity in the assay system used. The results in Table 15 show that the new cytokinin mesylate salts led to an increase of the cytokinin activity in the callus bioassay in comparison to the classical cytokinin free bases.

TABLE 15

The effect of cytokinin bases and cytokinin mesylate salts on growth of cytokinin-dependent tobacco callus *Nicotiana tabacum* L. cv. Wisconsins 38

| Tested compound | concentration with highest activity (mol · $l^{-1}$) | activity (%) [$10^{-5}$ mol · $l^{-1}$ BAP = 100%] |
|---|---|---|
| 1. 6-benzylaminopurine (BAP) | $10^{-6}$ | 100 (±13) |
| 2. BAP mesylate | $10^{-6}$ | 104 (±11) |
| 3. 6-(2-hydroxybenzylamino)purine - ortho-topolin (oT) | $10^{-6}$ | 86 (±15) |
| 4. oT mesylate | $10^{-6}$ | 87 (±16) |
| 5. 6-(3-hydroxybenzylamino)purine - meta-topolin (oT) | $10^{-6}$ | 105 (±23) |
| 6. mT mesylate | $10^{-6}$ | 111 (±21) |
| 7. Isopentenyladenine (iP) | $10^{-6}$ | 93 (±14) |
| 8. iP mesylate | $10^{-6}$ | 95 (±17) |
| 9. Dihydrozeatin (DHZ) | $10^{-6}$ | 78 (±18) |
| 10. DHZ mesylate | $10^{-6}$ | 78 (±21) |
| 11. trans-zeatin (tZ) | $10^{-6}$ | 109 (±21) |
| 12. tZ mesylate | $10^{-6}$ | 111 (±22) |
| 13. 2FBAP | $10^{-6}$ | 111 (±21) |
| 14. 2FBAP mesylate | $10^{-6}$ | 110 (±15) |
| 15. 3FBAP | $10^{-5}$ | 135 (±8) |
| 16. 3FBAP mesylate | $10^{-5}$ | 137 (±15) |
| 17. 4FBAP | $10^{-6}$ | 122 (±12) |
| 18. 4FBAP mesylate | $10^{-6}$ | 126 (±16) |
| 19. 2ClBAP | $10^{-6}$ | 93 (±4) |
| 20. 2ClBAP mesylate | $10^{-6}$ | 97 (±6) |
| 21. 3ClBAP | $10^{-5}$ | 94 (±6) |
| 22. 3ClBAP mesylate | $10^{-5}$ | 101 (±12) |
| 23. 2MeOBAP | $10^{-5}$ | 79 (±5) |
| 24. 2MeOBAP mesylate | $10^{-5}$ | 82 (±8) |
| 25. 3MeOBAP | $10^{-6}$ | 76 (±20) |
| 26. 3MeOBAP mesylate | $10^{-6}$ | 83 (±14) |
| 27. 2MBAP | $10^{-6}$ | 118 (±3) |
| 28. 2MBAP mesylate | $10^{-6}$ | 121 (±11) |

Example 21: The Effect of New Derivatives on In Vitro and Post Vitro Multiplication and Rooting of Rose (*Rosa multiflora*)

The aim of this experiment was to test whether the new compounds are of practical use in tissue culture practice. The multiplication rate was investigated and the post vitro effects on rooting were examined *Rosa hybrida* (pot rose cultivar) was cultured in 350 ml vessels with a screw on polycarbonate lid. Each culture vessel contained 100 ml autoclaved medium (120° C., 20 min). The cultures were maintained at 23±2° C. under a 16 h photoperiod at 40 $\mu M \cdot m^{-2}$ $s^{-1}$ PAR. The basal medium (BMR) contained Murashige and Skoog (1962) macroelements, microelements and vitamins, 95 μM NaFeEDTA, 555 μM myo-inositol, 111 mM sucrose, 1.332 mM glycine, 684 μM L-glutamine and 7 g/l agar. This medium was supplemented with 10 μM BAP, mT, or 3MeOBAP, or the corresponding mesylate salts. The control medium didn't contain any cytokinin After a culture period of 8 weeks, the number of induced shoots per explant was determined, as well as root number/explant and total root length/explant. The roots were removed and the explants (shoot clusters) were planted in unfertilised peat. After four weeks of acclimatising in a fog unit, root number and root length was determined. As expected, a cytokinin free medium yielded almost no new shoots. The original shoot explant grew out as a good quality single shoot that rooted very well. BAP gave a high shoot multiplication rate, but the shoots rooted badly (Table 16). Explants growing on cytokininin mesylates were characterized by a high multiplication index (a large number of new shoots) and were more rooted in comparison with free bases. The use of cytokinin mesylates led to an increase in all monitored parameters in plant culture compared to free cytokinin bases.

TABLE 16

The influence of mesylates on in vitro and post vitro multiplication and rooting of rose *Rosa multiflora*.

| | In vitro | | | | Ex vitro | |
|---|---|---|---|---|---|---|
| Cytokinin | Number of new shoots per explant | number of flowers per explant | Number of roots per explant | Overall length of explant (cm) | Number of roots per plant | Overall length of plant (cm) |
| control | 0.2 | 0.03 | 0.8 | 1.2 | 4.6 | 17.1 |
| 6-benzylaminopurine | 3.8 | 0.00 | 0.0 | 0.0 | 0.6 | 1.1 |
| 6-benzylaminopurine mesylate | 4.1 | 0.00 | 0.0 | 0.0 | 0.9 | 1.4 |
| 6-(3-hydroxybenzylamino)purine | 2.1 | 0.16 | 0.0 | 0.0 | 1.4 | 3.8 |
| 6-(3-hydroxyamino)purine mesylate | 2.4 | 0.17 | 0.0 | 0.0 | 1.8 | 4.3 |
| 6-(3-methoxybenzylamino)purine | 4.3 | 0.03 | 0.0 | 0.0 | 1.7 | 4.1 |
| 6-(3-methoxybenzylamino)purine mesylate | 4.5 | 0.02 | 0.0 | 0.0 | 1.9 | 4.5 |

Example 22: Increase in Grain Yield and Number of Productive Tillers of Spring Barley (Var. Francin)

Spring barley (variety Francin) was treated in 2019 at the locality in Olomouc, sprayed with substances—marked BAP (benzylaminopurine), meta-topolin mesylate and BAP mesylate. The seed was 3.5 million germinating seeds, the experiment was established in 5 randomized replicates for each variant, the control was an untreated variant. The experiment was performed according to the GEP (Good Experimental Practice) methodology, the size of individual plots was 10 $m^2$. The application of the substances was carried out at a rate of 300 l/ha, in the growth phase BBCH 31-33 (beginning of peeling). The concentration of test substances in the spray bed was 5 The results are summarized in Table 17.

TABLE 17

The influence of BAP, meta-topolin mesylate and BAP mesylate on spring barley

| | Control (untreated) | BAP (positive control) 5 uMol BBCH 31-33 | m-topolin mesylate 5 uMol BBCH 31-33 | BAP mesylate 5 uMol BBCH 31-33 |
|---|---|---|---|---|
| | | Compound name (variant) concentration application (BBCH) | | |
| Grain yield (t/ha) at 14% humidity | 7.42 | 7.42 | 8.01 | 7.74 |
| % compared to control | 100 | 100.13 | 108.03 | 104.34 |
| T-Test | | 0.747 | 0.443 | 0.418 |
| Strong tillers (number) | 1.8 | 2.8 | 2.45 | 2.75 |
| % compared to control | 100 | 155.56 | 136.11 | 152.78 |
| T-Test | | 0.001 | 0.018 | 0.001 |
| Medium tillers (number) | 2.1 | 1.7 | 1.25 | 1.35 |
| % compared to control | 100 | 80.95 | 59.52 | 64.29 |
| T-Test | | 0.149 | 0.008 | 0.004 |
| Weak tillers (number) | 1.85 | 2.1 | 1.8 | 2.25 |
| % compared to control | 100 | 113.51 | 97.3 | 121.62 |
| T-Test | | 0.534 | 0.878 | 0.165 |
| SUM of tillers | 5.75 | 6.6 | 5.5 | 6.35 |
| % compared to control | 100 | 114.78 | 95.65 | 110.43 |
| T-Test | | 0.069 | 0.581 | 0.134 |
| Length of plants | 82.8 | 82.5 | 83.1 | 83.2 |
| % compared to control | 100 | 99.64 | 100.36 | 100.48 |
| T-Test | | * | * | * |
| Number of spikes per square meter | 676.8 | 752 | 721.6 | 758.4 |
| % compared to control | 100 | 111.11 | 106.62 | 112.06 |
| T-Test | | 0.15 | 0.39 | 0.094 |

Foliar application of all new cytokinin derivatives increased number of strong (productive) tillers (from 36.11 to 55.56% over control), while number of medium tillers decreased. Grain yield were increased only in case of meta-topolin mesylate and BAP mesylate (108.03 and 104.34% at control). BAP used as positive control did not affect grain yield. In all test variants, the density of plants increased, too (106.62-112.06% compared at control).

The invention claimed is:

1. A compound in crystalline form, selected from the group consisting of:

crystalline form of benzylaminopurine mesylate having characteristic peaks in XRPD obtained using CuKα radiation: 6.2; 10.0; 15.2; 15.7; 18.6; 18.8; 19.3; 20.4; 23.5; 23.8; 24.4; 27.6±0.2° 2-theta;

crystalline meta-topolin mesylate having characteristic peaks in XRPD obtained using CuKα radiation: 8.1; 9.7; 13.1; 15.6; 16.8; 17.6; 19.1; 19.5; 22.2; 24.6; 24.8; 24.9; 25.7±0.2° 2-theta;

crystalline ortho-topolin mesylate having characteristic peaks in XRPD obtained using CuKα radiation: 9.8; 12.1; 16.8; 17.8; 18.3; 18.3; 20.7; 23.3; 24.1; 25.1; 26.8±0.2° 2-theta; and crystalline kinetin mesylate having characteristic peaksin XRPD obtained using CuKα radiation: 6.2; 18.9; 19.8; 20.4; 22.6; 23.9; 27.7; 27.8±0.2° 2-theta.

2. A method for protection of plant cells in vivo and in vitro against oxidative and/or electrophilic stress, and/or as antioxidants for the inhibition of lipid, protein and DNA peroxidation in plants in vivo or in vitro comprising the step of applying the compounds in crystalline form according to claim 1 to plants.

3. An agricultural and/or biotechnological preparation containing at least one compound in crystalline form according to claim 1, and at least one carrier and/or excipient.

* * * * *